US008222259B2

(12) United States Patent
Harris et al.

(10) Patent No.: US 8,222,259 B2
(45) Date of Patent: Jul. 17, 2012

(54) 1,2,4-TRIAZOLO[4,3-C]PYRIMIDIN-3-ONE AND PYRAZOLO[4,3-E]-1,2,4-TRIAZOLO[4,3-C]PYRIMIDIN-3-ONE COMPOUNDS FOR USE AS ADENOSINE $A_{2a}$ RECEPTOR ANTAGONISTS

(75) Inventors: Joel M. Harris, Kenilworth, NJ (US); Bernard R. Neustadt, Kenilworth, NJ (US); Jinsong Hao, Kenilworth, NJ (US); Andrew W. Stamford, Kenilworth, NJ (US)

(73) Assignee: Schering Corporation, Rahway, NJ (US)

( * ) Notice: Subject to any disclaimer, the term of this patent is extended or adjusted under 35 U.S.C. 154(b) by 0 days.

(21) Appl. No.: 12/920,924

(22) PCT Filed: Mar. 3, 2009

(86) PCT No.: PCT/US2009/035839
§ 371 (c)(1),
(2), (4) Date: Jan. 7, 2011

(87) PCT Pub. No.: WO2009/111449
PCT Pub. Date: Sep. 11, 2009

(65) Prior Publication Data
US 2011/0152256 A1  Jun. 23, 2011

Related U.S. Application Data

(60) Provisional application No. 61/033,477, filed on Mar. 4, 2008.

(51) Int. Cl.
C07D 487/12 (2006.01)
C07D 487/14 (2006.01)
C07D 487/04 (2006.01)
A61K 31/519 (2006.01)

(52) U.S. Cl. ............ 514/257; 514/262.1; 514/267; 544/256; 544/251; 544/247

(58) Field of Classification Search ............ None
See application file for complete search history.

(56) References Cited

U.S. PATENT DOCUMENTS

| 5,565,460 | A | 10/1996 | Suzuki |
| 6,867,217 | B1 | 3/2005 | South et al. |
| 7,452,892 | B2 * | 11/2008 | Wu et al. ............ 514/259.5 |
| 2005/0239795 | A1 | 10/2005 | Neustadt et al. |
| 2007/0066620 | A1 | 3/2007 | Neustadt |

FOREIGN PATENT DOCUMENTS

| WO | 9501356 | 1/1995 |
| WO | 9705138 | 2/1997 |
| WO | 9852568 | 11/1998 |
| WO | 0192264 | 12/2001 |
| WO | 02055083 | 7/2002 |
| WO | 03032996 | 4/2003 |
| WO | 2005044245 | 5/2005 |
| WO | 2005103055 | 11/2005 |
| WO | 2006138734 | 12/2006 |
| WO | 2007035542 | 3/2007 |
| WO | 2008002596 | 1/2008 |

OTHER PUBLICATIONS

Solid-State Chemistry of Drugs, 2d, Chapter 11:Hydrates and Solvates, 233 247 (1999).*
Rouhi, A.M., Chem. & Eng. News, Feb. 24, 2003, 81(8), 32-35.*
Morissette, et al. Adv. Drug. Del. Rev. 56:275 (2004).*
Bioorg. Med. Chem. Lett., 15: 3670-3674 (2005).
Bioorg. Med. Chem. Lett., 15:3675-3678 (2005).
Cocco, et al., Journal of Heterocyclic Chemistry, 29 (5), 1341-7 (1992).

* cited by examiner

Primary Examiner — Yong Chu
Assistant Examiner — Michael Barker
(74) Attorney, Agent, or Firm — H. Eric Fischer; Gerard M. Devlin

(57) ABSTRACT

Compounds of the Formula I wherein $R^1$ and $R^2$ together with the carbon atoms to which they are bonded optionally form a further heteroaromatic ring of the formula (II) as well as pharmaceutically acceptable salts, solvates, esters and prodrugs thereof are adenosine A2a receptor antagonists and, therefore, are useful in the treatment of central nervous system diseases, in particular Parkinson's disease.

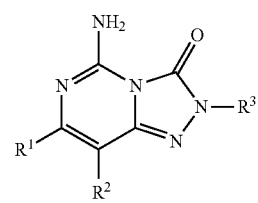

(I)

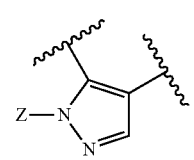

(II)

21 Claims, No Drawings

1,2,4-TRIAZOLO[4,3-C]PYRIMIDIN-3-ONE AND PYRAZOLO[4,3-E]-1,2,4-TRIAZOLO[4,3-C]PYRIMIDIN-3-ONE COMPOUNDS FOR USE AS ADENOSINE $A_{2a}$ RECEPTOR ANTAGONISTS

BACKGROUND OF THE INVENTION

1. Field of the Invention

The present invention relates to 1,2,4-triazolo[4,3-c]pyrimidin-3-one and pyrazolo[4,3-e]-1,2,4-triazolo[4,3-c]pyrimidine-3-one adenosine $A_{2a}$ receptor antagonist compounds, methods of using said compounds in the treatment of central nervous system diseases, in particular Parkinson's disease, and to pharmaceutical compositions comprising said compounds.

2. Description of Related Art

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity.

Triazolo-pyrimidine adenosine $A_{2a}$ receptor antagonists have been disclosed previously, for example in WO 95/01356; U.S. Pat. No. 5,565,460; WO 97/05138; WO 98/52568; WO 01/92264; PCT/US02/32630; filed Oct. 11, 2002; U.S. Pat. No. 6,897,217; US 20050239795A1; US 20070066620A1; WO05/103055; WO07/035,542A1; Bioorg. Med. Chem. Lett., 15: 3670-3674 (2005); and Bioorg. Med. Chem. Lett., 15: 3675-3678 (2005).

Adenosine $A_{2a}$ receptor antagonists have been disclosed as being useful in the treatment or prevention of Extra Pyramidal Syndrome, dystonia, restless leg syndrome (RLS) or periodic limb movement in sleep (PLMS) in PCT/US03/40456, filed Dec. 17, 2003, and have been disclosed as being useful in the treatment of attention deficit hyperactivity disorder (ADHD) in WO 02/055083.

SUMMARY OF THE INVENTION

The present invention relates to compounds of the structural Formula I:

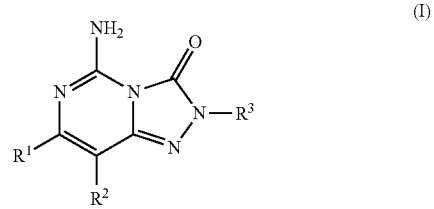

wherein:
$R^1$ represents aryl or heteroaryl; and
$R^2$ represents hydrogen; or
$R^1$ and $R^2$ together with the carbon atoms to which they are bonded form a further heterocyclic ring of the formula:

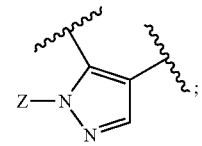

or a carbocyclic ring system of the formula:

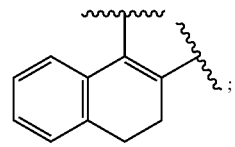

$R^3$ represents aryl, cycloalkylalkyl, aralkyl or heteroarylalkyl;
Z represents alkyl, alkenyl, haloalkyl, aminoalkyl, alkylaminoalkyl, dialkylaminoalkyl, aralkyl or $CH_2CH_2R^4$;
$R^4$ represents a heterocycle selected from the group consisting of:

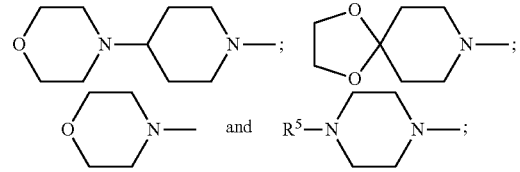

and
$R^5$ represents alkyl, alkoxycarbonyl, alkylsulfonyl, aryl or heteroaryl;
or a pharmaceutically acceptable salt, solvate, ester or prodrug thereof.

Another aspect of the invention is a pharmaceutical composition comprising a therapeutically effective amount of at least one compound of Formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, and stroke, comprising administering a therapeutically acceptable amount therefor of at least one compound of Formula I to a mammal in need of such treatment.

The invention also relates to a method of treating attention related disorders, such as attention deficit disorder (ADD) and attention deficit hyperactivity disorder (ADHD), comprising administering a therapeutically acceptable amount therefor of at least one compound of Formula I to a mammal in need of such treatment.

The invention also relates to a method of treating or preventing Extra-Pyramidal Syndrome (e.g., dystonia, akathisia, pseudoparkinsonism and tardive dyskinesia), of treating primary (idiopathic) dystonia, and of treating or preventing dystonia in patients who exhibit dystonia as a result of treatment with a tricyclic antidepressant, lithium or an anticonvulsant, or who have used cocaine, comprising administering a therapeutically acceptable amount therefor of at least one compound of Formula I to a mammal in need of such treatment.

The invention further relates to a method of treating abnormal movement disorders, such as restless leg syndrome (RLS) or periodic limb movement in sleep (PLMS), comprising administering to a patient in need thereof a therapeutically effective amount therefor of at least one compound of Formula I.

In particular, the invention is drawn to the method of treating Parkinson's disease comprising administering a therapeutically acceptable amount therefor of at least one compound of Formula I to a mammal in need of such treatment.

Still another aspect of the invention is a method of treating Parkinson's disease with a combination of a therapeutically acceptable amount therefor of at least one compound of Formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor.

The invention further relates to a pharmaceutical composition comprising a therapeutically acceptable amount of at least one compound of Formula I and one or more agents known to be useful in the treatment of Parkinson's disease in a pharmaceutically acceptable carrier.

The invention also comprises a method of treating RLS or PLMS comprising administering to a patient in need thereof a therapeutically acceptable amount of a combination of at least one compound of Formula I with another agent useful in treating RLS or PLMS, such as levodopa/carbidopa, levodopa/benserazide, a dopamine agonist, a benzodiazepine, an opioid, an anticonvulsant or iron.

DETAILED DESCRIPTION OF THE INVENTION

In one preferred embodiment, the compound of Formula I or pharmaceutically acceptable salt, solvate, ester or prodrug thereof is one wherein $R^1$ represents aryl; and $R^2$ represents hydrogen.

In another preferred embodiment, the compound of Formula I or pharmaceutically acceptable salt, solvate, ester or prodrug thereof is one wherein $R^1$ and $R^2$ together with the carbon atoms to which they are bonded form a further heteroaromatic ring of the formula:

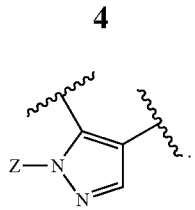

In another preferred embodiment, the compound of Formula I or pharmaceutically acceptable salt, solvate, ester or prodrug thereof is one wherein $R^1$ and $R^2$ together with the carbon atoms to which they are bonded form a carbocyclic ring system of the formula:

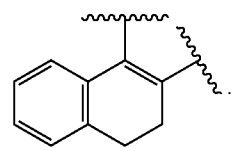

In an especially preferred embodiment, the compound of Formula I or pharmaceutically acceptable salt, solvate, ester or prodrug thereof is one wherein:
  $R^1$ represents aryl; and
  $R^2$ represents hydrogen; or
  $R^1$ and $R^2$ together with the carbon atoms to which they are bonded form a further heteroaromatic ring of the formula:

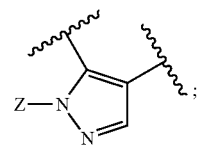

or a carbocyclic ring system of the formula:

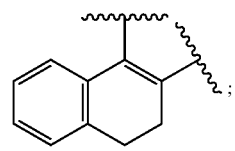

$R^3$ represents aralkyl; and
Z represents alkenyl or haloalkyl.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, 2-propynyl, 2-butynyl and 3-methyl-1-butynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), $Y_1Y_2N$—, $Y_1Y_2$N-alkyl-, $Y_1Y_2$NC(O)—, $Y_1Y_2NSO_2$— and, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

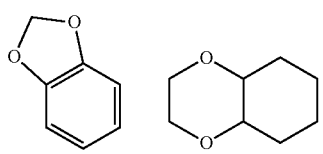 

and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also include a single moiety (e.g., carbonyl) which simultaneously replaces two available hydrogens on the same carbon atom on a ring system. Examples of such moiety are 2-pyrrolidone:

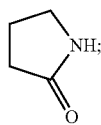

and 3-pyrrolidone:

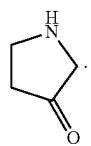

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, 7-oxabicyclo[2.2.1]heptenyl, dihydrothiophenyl, dihydrothiopyranyl, and the like. "Heterocyclenyl" may also include a single moiety (e.g., carbonyl) which simultaneously replaces two available hydrogens on the same carbon atom on a ring system. An example of such moiety is 1,2-dihydro-pyrrol-3-one:

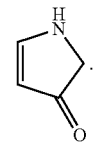

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

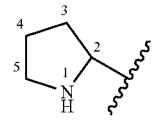

there is no —OH attached directly to carbons marked 2 and 5.

It should also be noted that tautomeric forms such as, for example, the moieties:

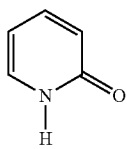 and 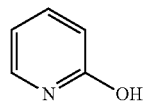

are considered equivalent in certain embodiments of this invention.

"Alkynylalkyl" means an'alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "pharmaceutical composition" means a composition, as defined above, in a form and comprising active ingredients, vehicles, carriers and/or auxiliaries suitable for pharmaceutical use.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-$(C_1$-$C_2)$alkyl and piperidino-, pyrrolidino- or morpholino$(C_2$-$C_3)$alkyl, and the like.

Similarly, if a compound of Formula I contains an alcohol functional group, a prodrug can be formed by the replacement of the hydrogen atom of the alcohol group with a group such as, for example, $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6)$alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$alkyl, $(C_3$-$C_7)$cycloalkyl, benzyl, or R-carbonyl is a natural α-aminoacyl or natural α-aminoacyl, —CH(OH)C(O)OY$^1$ wherein Y$^1$ is H, $(C_1$-$C_6)$alkyl or benzyl, —CH(OY$^2$)Y$^3$ wherein Y$^2$ is $(C_1$-$C_4)$alkyl and Y$^3$ is $(C_1$-$C_6)$alkyl, carboxy $(C_1$-$C_6)$alkyl, amino $(C_1$-$C_4)$alkyl or mono-N— or di-N,N—$(C_1$-$C_6)$alkylaminoalkyl, —CH(Y$^4$)Y$^5$ wherein Y$^4$ is H or methyl and Y$^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, methyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino alcohol). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

In general, the compounds of this invention may be prepared from known or readily prepared starting materials, following methods known to one skilled in the art of organic synthesis. Methods useful for making the [1,2,4]triazolo[4,3-c]pyrimidin-3-one derivatives are set forth in the Examples below and generalized in Schemes 1-3. Alternative synthetic pathways and analogous structures will be apparent to those skilled in the art of organic synthesis. All stereoisomers and tautomeric forms of the compounds are contemplated.

The preparation of compounds of structure E is illustrated in Scheme 1. Suzuki coupling of dichloride A with various boronic acids provides pyrimidines B. Subsequent chloride displacement with hydrazine yields pyrimidine C. Condensation of pyrimidine C with various aldehydes and reduction with sodium cyanoborohydride gives pyrimidine D. Treatment of compound D with phosgene provides compounds with the general structure E.

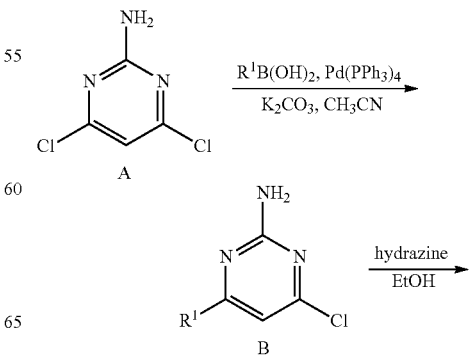

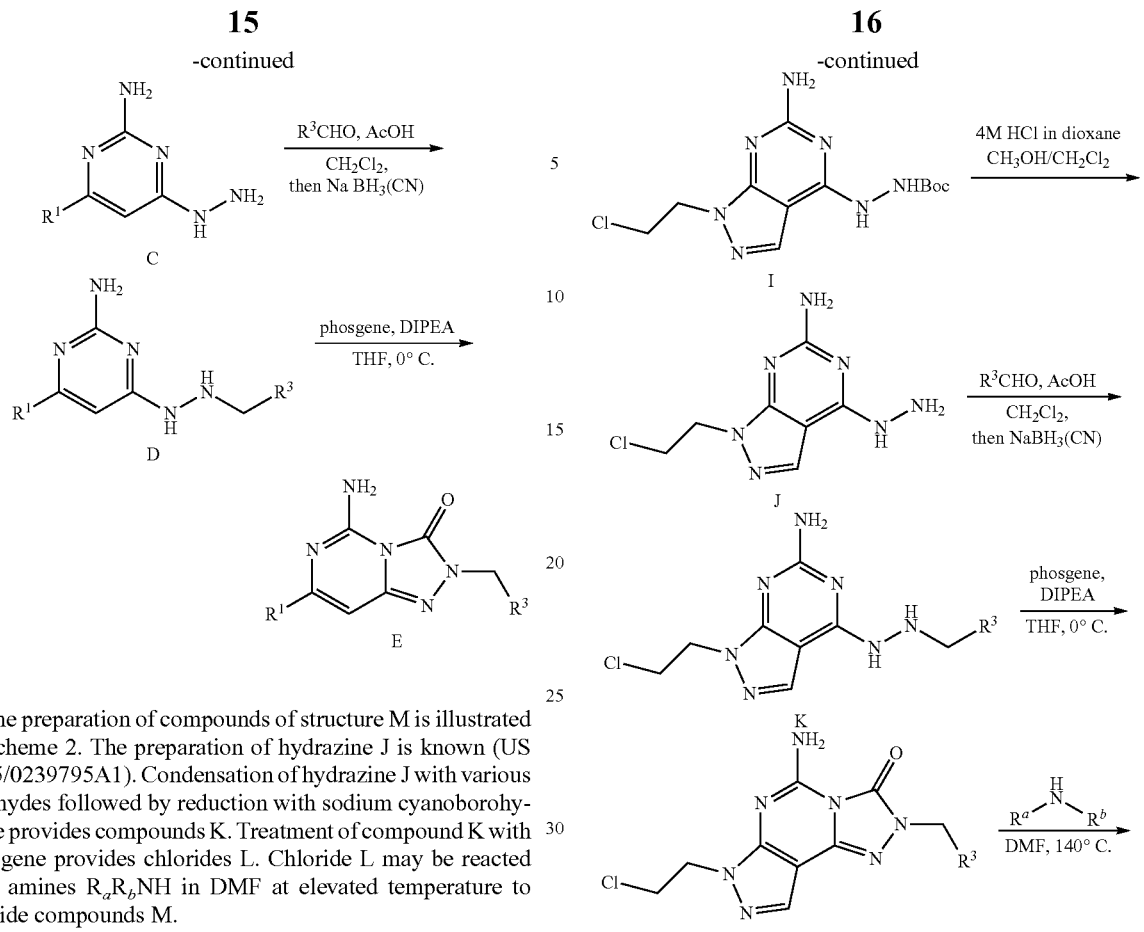

The preparation of compounds of structure M is illustrated in Scheme 2. The preparation of hydrazine J is known (US 2005/0239795A1). Condensation of hydrazine J with various aldehydes followed by reduction with sodium cyanoborohydride provides compounds K. Treatment of compound K with phosgene provides chlorides L. Chloride L may be reacted with amines $R_aR_bNH$ in DMF at elevated temperature to provide compounds M.

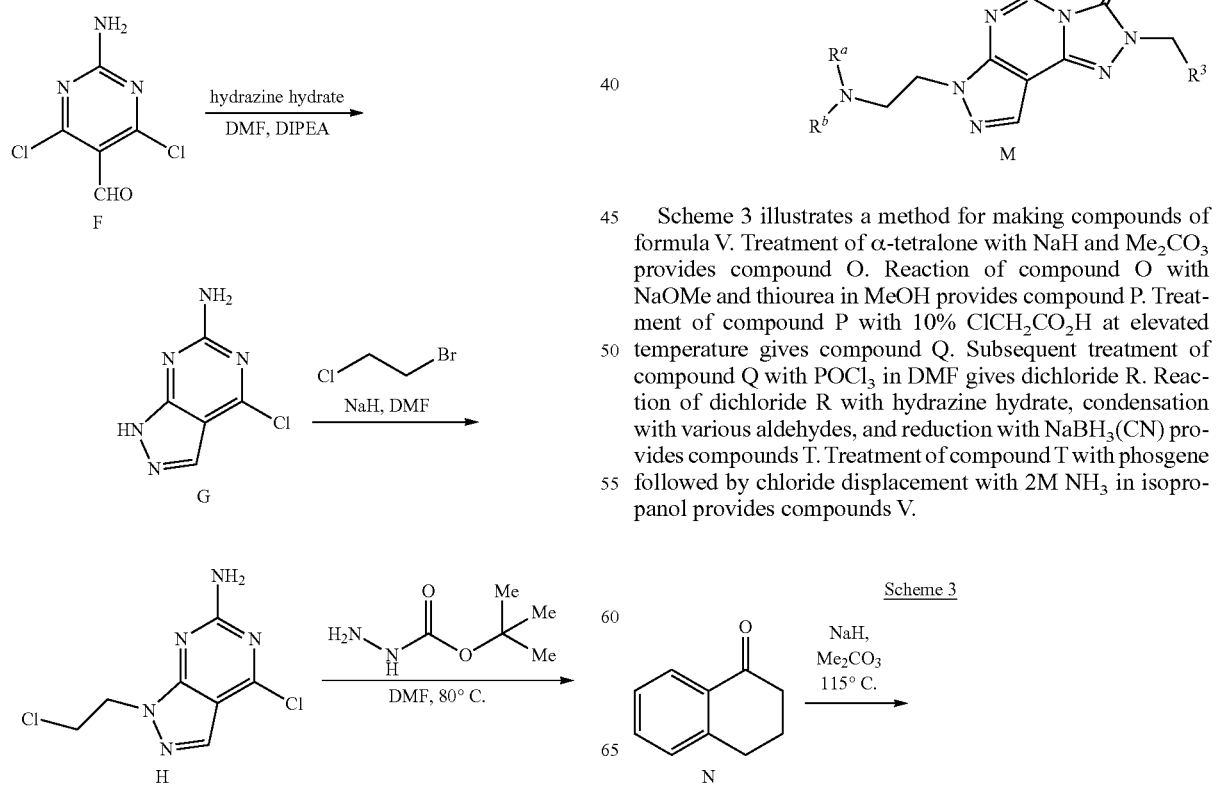

Scheme 3 illustrates a method for making compounds of formula V. Treatment of α-tetralone with NaH and $Me_2CO_3$ provides compound O. Reaction of compound O with NaOMe and thiourea in MeOH provides compound P. Treatment of compound P with 10% $ClCH_2CO_2H$ at elevated temperature gives compound Q. Subsequent treatment of compound Q with $POCl_3$ in DMF gives dichloride R. Reaction of dichloride R with hydrazine hydrate, condensation with various aldehydes, and reduction with $NaBH_3(CN)$ provides compounds T. Treatment of compound T with phosgene followed by chloride displacement with 2M $NH_3$ in isopropanol provides compounds V.

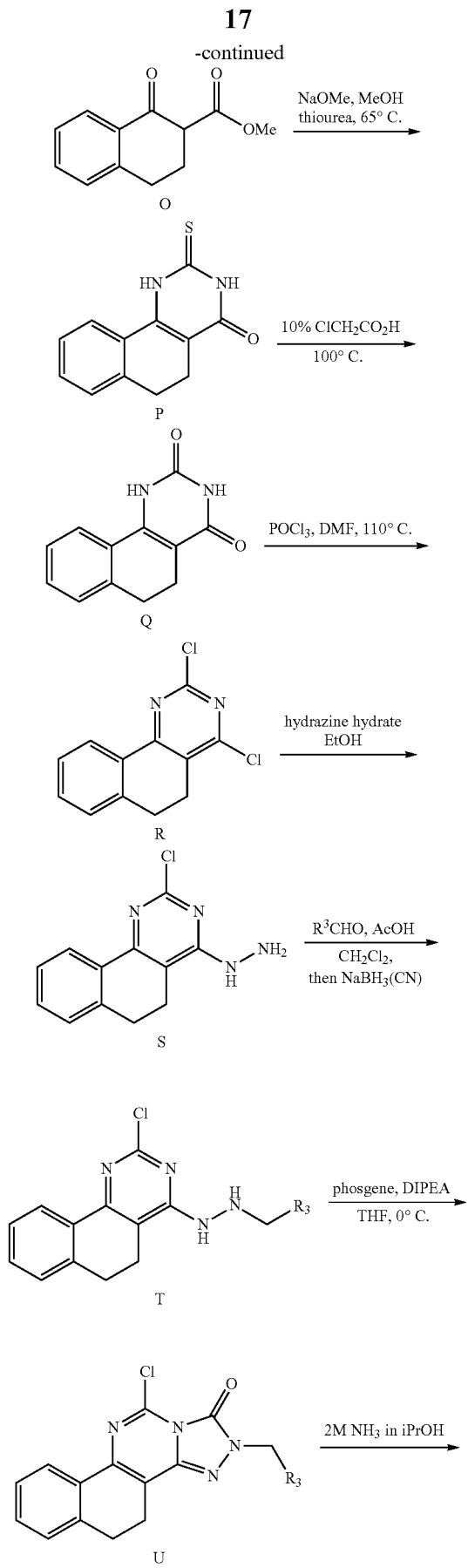

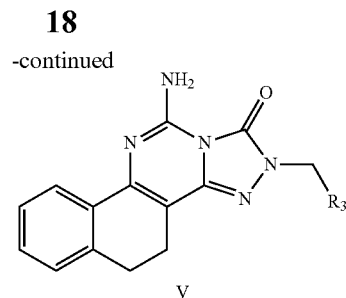

The starting materials and reagents depicted in Schemes 1-3 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of compounds of Formula I may require protection of certain functional groups (i.e., derivatization for the purpose of chemical compatibility with a particular reaction condition). Suitable protecting groups for the various functional groups of the compounds of Formula I and methods for their installation and removal may be found in Greene et. al., *Protective Groups in Organic Synthesis*, Wiley-Interscience, New York, (1999).

EXAMPLES

The following examples constitute illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. Microwave reactions were performed using the Biotage Initiator microwave. $^1$H NMR spectra were obtained on a Gemini AS-400 (400 MHz) and are reported as ppm downfield from Me$_4$Si with number of protons, multiplicities, and coupling constants in Hertz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion is given.

The following solvents and reagents may be referred to by their abbreviations:
Me=methyl; Et=ethyl; Pr=propyl; Bu=butyl; Ph=phenyl, and Ac=acetyl
μl=microliters
EtOAc=ethyl acetate
AcOH or HOAc=acetic acid
Atm=atmosphere
BINAP=rac-2,2'-bis(diphenylphosphino)-1,1'-binaphthyl
Boc or BOC=tert-butoxycarbonyl
BSA=N,O-(bistrimethylsilyl)acetamide
CH$_2$Cl$_2$=dichloromethane
DIPEA=diisoproylethylamine
DMAP=4-dimethylaminopyridine
DMF=dimethylformamide
DMSO=dimethylsulfoxide EDCI=1-(3-dimethylaminopropyl)-3-ethylcarbodiimide
EDTA=ethylenediaminetetraacetic acid
EtOH=ethanol
g=grams
h=hour
HOBt=1-hydroxybenzotriazole
LAH=lithium aluminum hydride
LCMS or LC/MS=liquid chromatography mass spectrometry
min=minute
mg=milligrams
mL=milliliters
mmol=millimoles
mCPBA=3-chloroperoxybenzoic acid
MeOH=methanol
MS=mass spectrometry
NMR=nuclear magnetic resonance spectrometry
RT or rt=room temperature (ambient, about 25° C.)
TEA or Et$_3$N=triethylamine
TFA=trifluoroacetic acid
THF=tetrahydrofuran
TLC=thin layer chromatography
TMS=trimethylsilyl
TMSOTf=trimethylsilyl trifluoromethanesulfonate
TBS=tert-butyldimethylsilyl
X-Phos=2-dicyclohexylphosphino-2',4',6'-triisopropylbiphenyl In general, the compounds of this invention may be prepared from known or readily prepared starting materials, following methods known to one skilled in the art of organic synthesis. All stereoisomers and tautomeric forms of the compounds are contemplated.

Example 1

Preparation of Compound 1

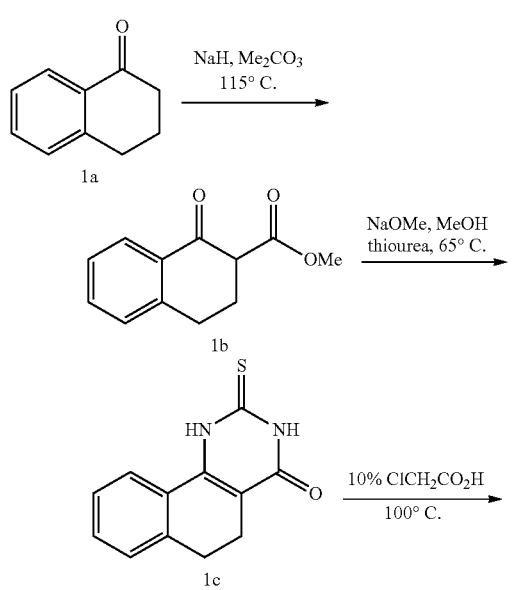

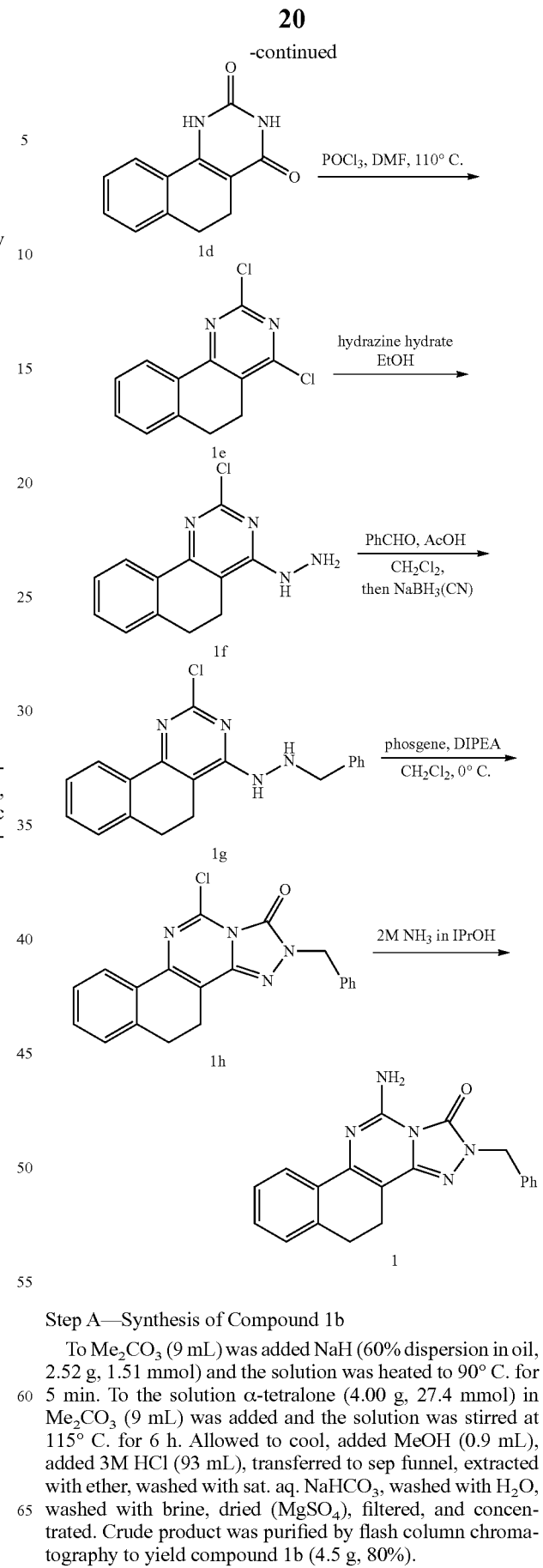

Step A—Synthesis of Compound 1b

To Me$_2$CO$_3$ (9 mL) was added NaH (60% dispersion in oil, 2.52 g, 1.51 mmol) and the solution was heated to 90° C. for 5 min. To the solution α-tetralone (4.00 g, 27.4 mmol) in Me$_2$CO$_3$ (9 mL) was added and the solution was stirred at 115° C. for 6 h. Allowed to cool, added MeOH (0.9 mL), added 3M HCl (93 mL), transferred to sep funnel, extracted with ether, washed with sat. aq. NaHCO$_3$, washed with H$_2$O, washed with brine, dried (MgSO$_4$), filtered, and concentrated. Crude product was purified by flash column chromatography to yield compound 1b (4.5 g, 80%).

Step B—Synthesis of Compound 1c

Sodium metal (0.62 g, 26.7 mmol) was added to MeOH (12 mL) and stirred for 30 min. Compound 1b (2.2 g, 10.8 mmol) in MeOH (15 mL) was added and thiourea (0.90 g, 11.8 mmol) was added and the solution was heated to 70° C. for 12 h. Allowed reaction to cool and concentrated under vacuum. To the solid was added $H_2O$ (100 mL), acidified to pH=5 with AcOH, filtered solid, rinsed solid with sat. aq. $NaHCO_3$, rinsed with $H_2O$, and dried to give compound 1c (0.56 g, 22%).

Step C—Synthesis of Compound 1d

To the product of Step B (0.56 g, 2.4 mmol) was added 10% $ClCH_2CO_2H$ (60 mL) and the solution was heated to 105° C. for 12 h. Allowed to cool, filtered off solid, rinsed with 95% ethanol, rinsed with ether, and dried to give compound 1d (0.20 g, 38%).

Step D—Synthesis of Compound 1e

To the product of Step C (0.20 g, 0.93 mmol) was added $POCl_3$ (15 mL) and 5 drops of DMF. The solution was heated to 110° C. for 46 h. Allowed to cool and concentrated under vacuum. Poured crude residue onto ice water and stirred for 20 min. Solution was partitioned between $CH_2Cl_2$ and $H_2O$, washed organic layer with brine, dried ($MgSO_4$), filtered, and concentrated to yield compound 1e.

Step E—Synthesis of Compound 1f

To compound 1e in EtOH (6 mL) was added hydrazine monohydrate (0.09 mL) and DMF (3 mL). The solution was stirred for 3 h. Filtered the reaction to provide compound 1f (0.24 g, 100%)

Step F—Synthesis of Compound 1g

To compound 1f (0.24 g, 0.90 mmol) was added benzaldehyde (0.104 mL, 1.4 mmol), AcOH (0.08 mL), and $CH_2Cl_2$ (30 mL). The solution was stirred for 30 min at room temperature and 45 min at 40° C. Allowed to cool, added $NaBH_3(CN)$ (0.18 g, 2.7 mmol) and the solution was heated to 40° C. for 43 h. Solution was partitioned between $CH_2Cl_2$ and $H_2O$, washed with brined, dried ($MgSO_4$), filtered and concentrated to give compound 1g (0.4 g, 100%).

Step G—Synthesis of Compound 1

To compound 1g (0.4 g, 0.90 mmol) was added $CH_2Cl_2$ (20 mL), DIPEA (0.52 mL, 2.3 mmol), and phosgene (20% in toluene, 1.12 mL, 1.6 mmol). The solution was stirred for 30 min at 0° C. and 10 min at room temperature. Triturated solid with MeOH, filtered, and dried to yield compound 1h. To compound 1h was added 2M $NH_3$ in isopropanol (15 mL) in a sealed tube, stirred and heated to 110° C. for 20 h. Allowed to cool, concentrated under vacuum, triturated with MeOH to give compound 1 as a white solid (0.12 g, 30%).

Example 2

Preparation of Compound 2

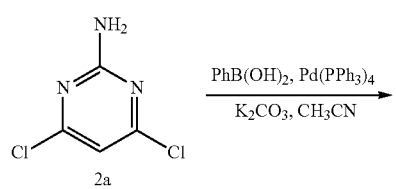

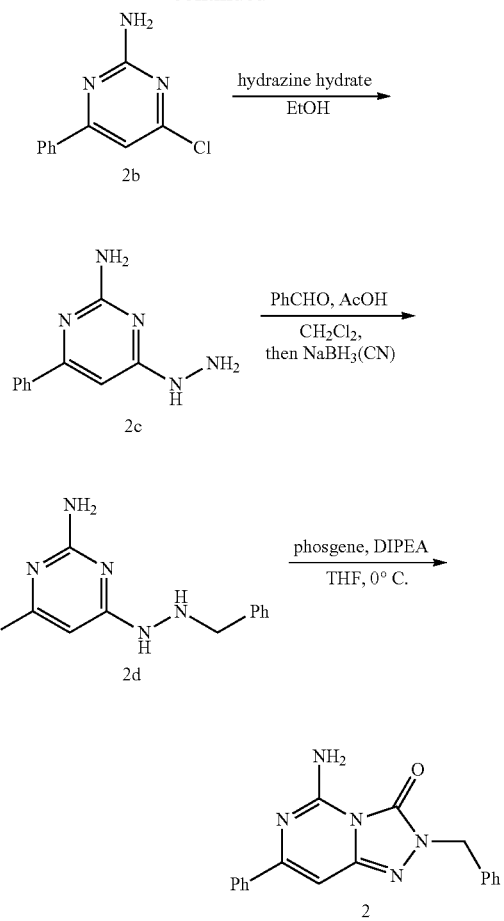

Step A—Synthesis of Compound 2b

To compound 2a (2.0 g, 12.2 mmol) was added $CH_3CN$ (40 mL), $K_2CO_3$ (2M solution, 6.1 mL, 12.2 mmol), $Pd(PPh_3)_4$ (0.35 g, 0.31 mmol), and $PhB(OH)_2$ (0.74 g, 6.1 mmol). The solution was stirred and heated to 90° C. for 4 h. Allowed to cool, transferred to sep. funnel, added $CH_2Cl_2$ (50 mL), added $H_2O$ (50 mL), mixed, separated, extracted aqueous layer with $CH_2Cl_2$, combined organic layers, dried ($MgSO_4$), filtered, and concentrated. Purified using preparative thin layer chromatography (100% $CH_2Cl_2$) to yield compound 2b (0.8 g, 64%).

Step B—Synthesis of Compound 2c

To compound 2b (0.8 g, 3.9 mmol) was added EtOH (40 mL) and hydrazine hydrate (0.38 mL, 7.78 mmol) and the solution was stirred for 24 h. Filtered solid, rinsed with MeOH, and dried to yield compound 2c (0.75 g, 96%).

Step C—Synthesis of Compound 2d

Using Step F from Example 1, substituting compound 2c for compound 1f, compound 2d was prepared.

Step D—Synthesis of Compound 2

To compound 2d (0.2 g, 0.69 mmol) was added THF (15 mL), DIPEA (0.24 mL, 1.37 mmol), and phosgene (20% solution in toluene, 0.73 mL, 1.37 mmol). The solution was stirred for 30 min. Transferred to sep. funnel, added $CH_2Cl_2$ (50 mL), added $H_2O$ (50 mL), mixed, separated, extracted aqueous layer with $CH_2Cl_2$, combined organic layers, dried

Example 3

Preparation of Compound 3

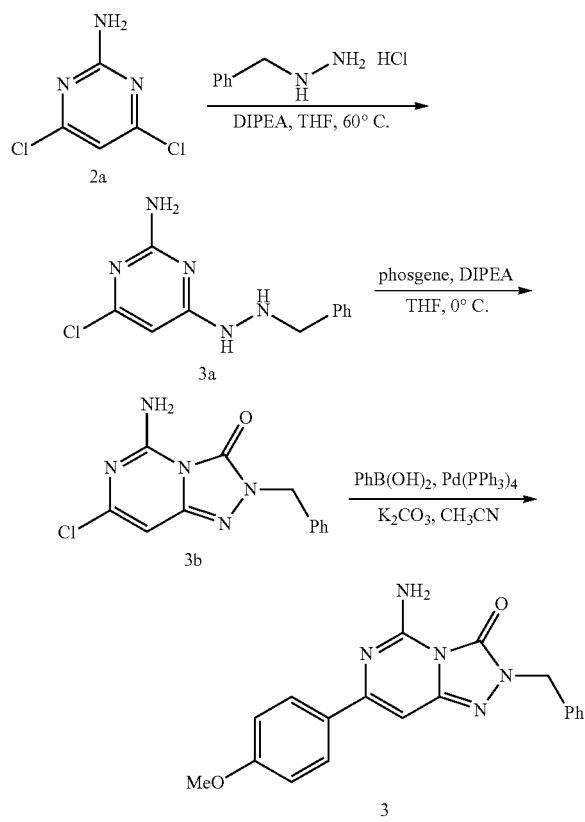

Step C—Synthesis of Compound 3

Using Step A from Example 2, substituting 4-methoxyphenylboronic acid for phenylboronic acid and substituting compound 3b for compound 2a, compound 3 was prepared.

Example 4

Preparation of Compound 4

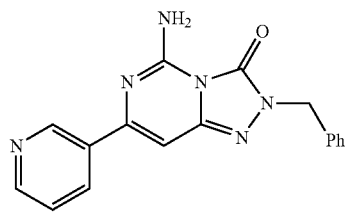

Compound 4 was synthesized using Step C described in Example 3, substituting 3-pyridylboronic acid for 4-methoxyphenylboronic acid.

Example 5

Preparation of Compound 7

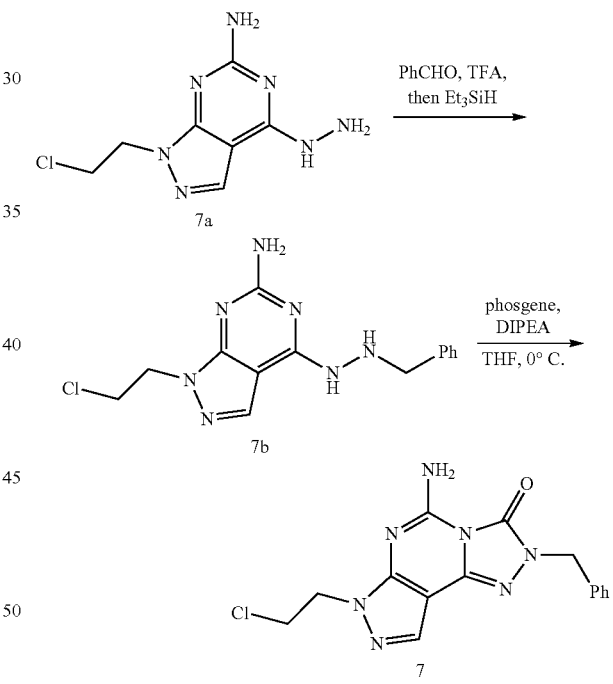

Step A—Synthesis of Compound 3a

To compound 2a (3.0 g, 18.3 mmol) was added THF (100 mL), DIPEA (15.9 mL, 91.5 mmol), and benzylhydrazine hydrochloride (3.9 g, 20.1 mmol). The solution was stirred at 60° C. for 3 h. Allowed to cool, transferred to sep. funnel, added $CH_2Cl_2$ (100 mL), added $H_2O$ (100 mL), mixed, separated, extracted aqueous layer with $CH_2Cl_2$, combined organic layers, dried ($MgSO_4$), filtered, and concentrated to yield compound 3a (4.4 g, 96%).

Step B—Synthesis of Compound 3b

To compound 3a (2.5 g, 10.0 mmol) was added THF (100 mL), DIPEA (5.2 mL, 30 mmol), and phosgene (20% solution in toluene, 8 mL, 15 mmol) and the solution was stirred at 0° C. for 1 h. Allowed to cool, transferred to sep. funnel, added $CH_2Cl_2$ (100 mL), added $H_2O$ (100 mL), mixed, separated, extracted aqueous layer with $CH_2Cl_2$, combined organic layers, dried ($MgSO_4$), filtered, and concentrated. Purified crude material by flash column chromatography using silica gel (1-5% $MeOH/CH_2Cl_2$) to provide compound 3b as a white solid (1.2 g, 44%).

Step A—Synthesis of Compound 7b

To compound 7a (preparation described in patent US 2005/0239795A1, 2.0 g, 8.8 mmol) was added TFA (30 mL) and benzaldehyde (0.99 mL, 9.7 mmol) and the solution was stirred for 30 min. To the solution was added $Et_3SiH$ (7.0 mL, 44 mmol) and the solution was stirred for 6 h. Added $H_2O$ (50 mL), $CH_2Cl_2$ (50 mL), and added conc. $NH_4OH$ until pH 10. Transferred to sep. funnel, added 300 mL EtOAc, $H_2O$ (100 mL), mixed, separated, extracted aqueous layer with EtOAc, combined organic layers, dried ($MgSO_4$), filtered, and concentrated to yield compound 7b (2.0 g, 72%).

Step B—Synthesis of Compound 7

Using Step B from Example 3, substituting compound 7b for compound 3a, compound 7 was prepared.

Example 6

Preparation of Compound 8

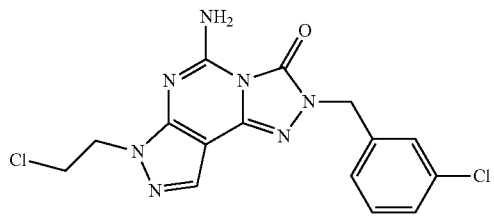

Compound 8 was synthesized using Steps A and B from Example 5, substituting 3-chlorobenzaldehyde for benzaldehyde.

Example 7

Preparation of Compound 28

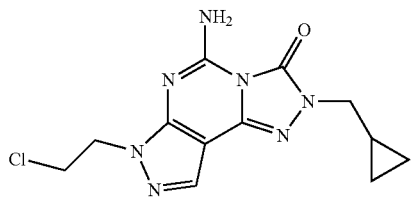

Compound 28 was synthesized using Steps A and B from Example 5, substituting cyclopropanecarbaldehyde for benzaldehyde.

Example 8

Preparation of Compound 6

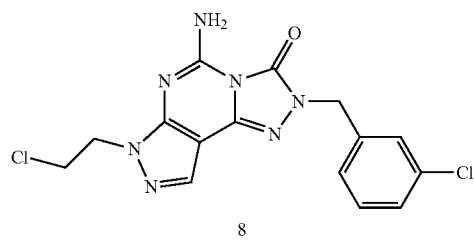

Step A—Synthesis of Compound 6

To compound 8 (150 mg, 0.40 mmol) was added DMF (1.5 mL), and DBU (0.12 mL, 0.80 mmol) and the solution was stirred and heated to 100° C. for 14 h. Allowed to cool, concentrated under vacuum, and purified by preparative TLC using (1% MeOH/CH$_2$Cl$_2$) to yield compound 6 (33 mg, 24%).

Example 9

Preparation of Compound 5

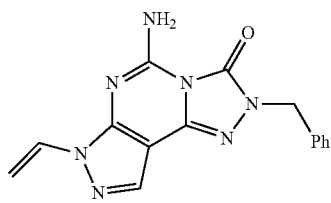

Compound 5 was synthesized using Step A from Example 8, substituting compound 7 for compound 8.

Example 10

Preparation of Compound 23

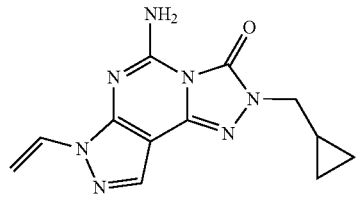

Compound 23 was synthesized using Step A from Example 8, substituting compound 28 for compound 8.

Example 11

Preparation of Compound 29

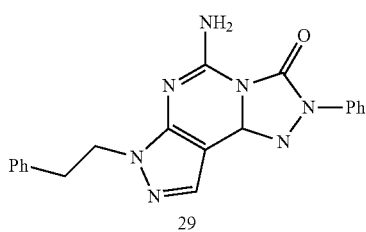

Using Steps A and B described in Example 3, substituting compound 29a (prepared using methods to prepare compound 7a, patent US 2005/0239795A) for compound 2a, and substituting phenyl hydrazine for benzylhydrazine hydrochloride, compound 29 was prepared.

Example 12

Preparation of Compound 27

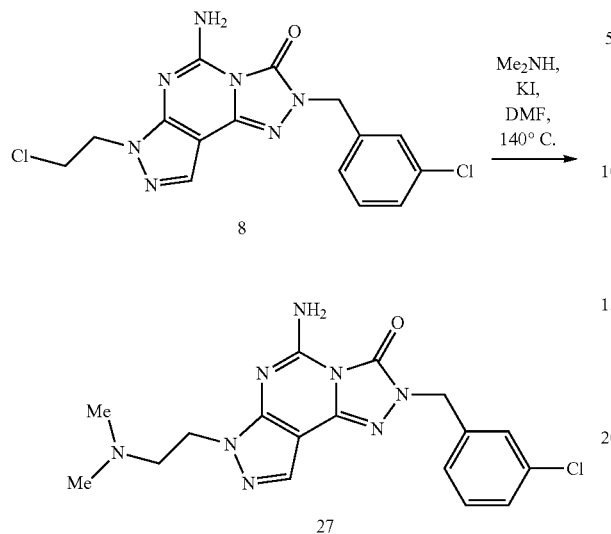

Step A—Synthesis of Compound 27

To compound 8 (100 mg, 0.26 mmol) was added DMF (3 mL), KI (44 mg, 0.26 mmol), and dimethylamine (40% in $H_2O$, 0.045 mL, 0.35 mmol). The solution was stirred at 140° C. for 14 h. Allowed to cool, concentrated under vacuum, and purified by preparative TLC using (5% $CH_3OH/CH_2Cl_2$) to yield compound 27 (11 mg, 11%).

Example 13

Preparation of Compound 9

Using Step A from Example 12, substituting compound 5 for compound 8 and substituting aryl-piperazine 9a (prepared in patent US 2005/0239795A) for dimethylamine, compound 9 was prepared.

Example 14

Preparation of Compound 10

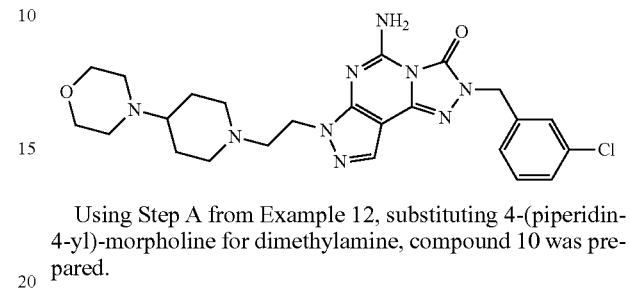

Using Step A from Example 12, substituting 4-(piperidin-4-yl)-morpholine for dimethylamine, compound 10 was prepared.

Example 15

Preparation of Compound 11

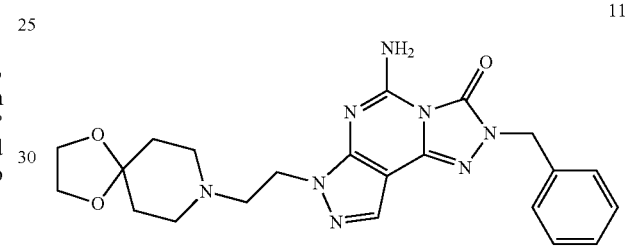

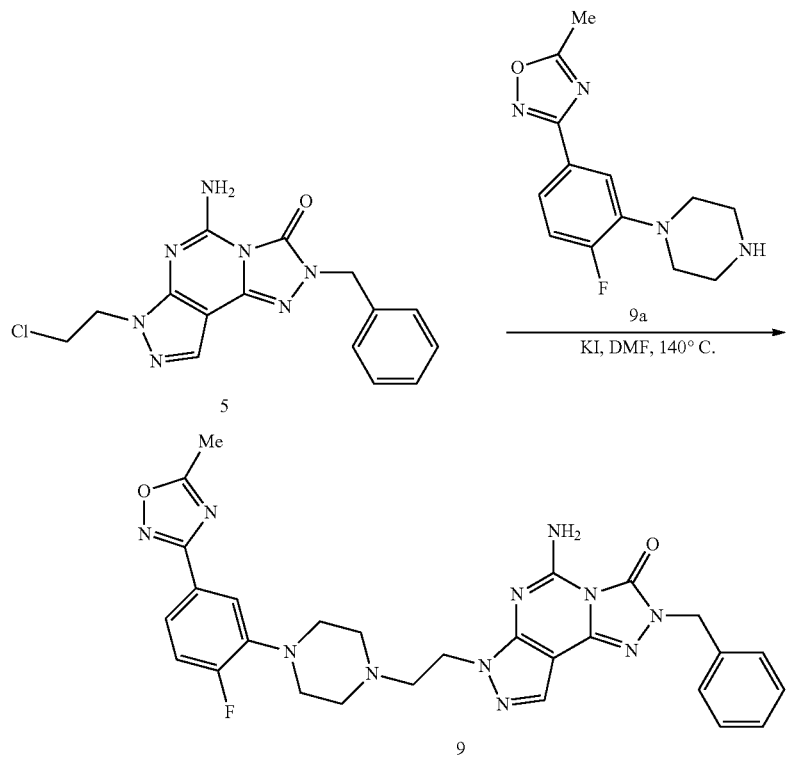

Using Step A from Example 12, substituting compound 5 for compound 8 and substituting 1,4-dioxa-8-azaspiro[4.5]decane for dimethylamine, compound 11 was prepared.

Example 16

Preparation of Compound 12

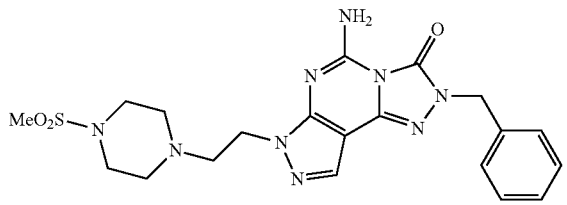

Using Step A from Example 12, substituting compound 5 for compound 8 and substituting 1-(methylsulfonyl)piperazine for dimethylamine, compound 12 was prepared.

Example 17

Preparation of Compound 13

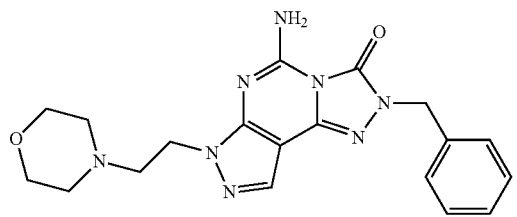

Using Step A from Example 12, substituting compound 5 for compound 8 and substituting morpholine for dimethylamine, compound 13 was prepared.

Example 18

Preparation of Compound 14

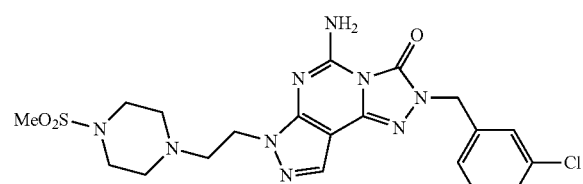

Using Step A from Example 12, substituting 1-(methylsulfonyl)piperazine for dimethylamine, compound 14 was prepared.

Example 19

Preparation of Compound 15

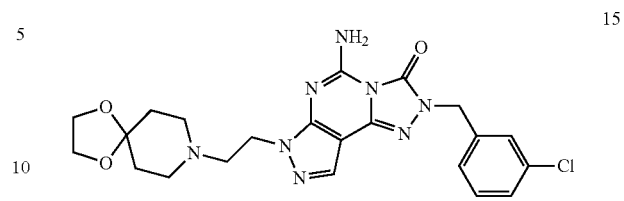

Using Step A from Example 12, substituting 1,4-dioxa-8-azaspiro[4.5]decane for dimethylamine, compound 15 was prepared.

Example 20

Preparation of Compound 16

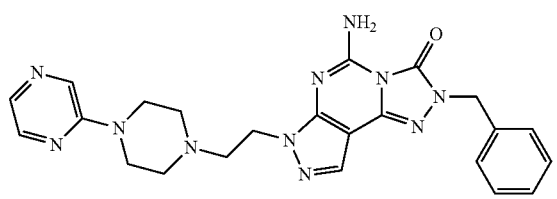

Using Step A from Example 12, substituting compound 5 for compound 8 and substituting 2-(piperazin-1-yl)pyrazine for dimethylamine, compound 16 was prepared.

Example 21

Preparation of Compound 17

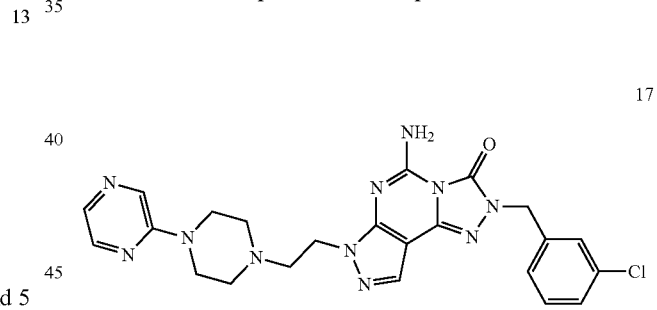

Using Step A from Example 12, substituting 2-(piperazin-1-yl)pyrazine for dimethylamine, compound 17 was prepared.

Example 22

Preparation of Compound 18

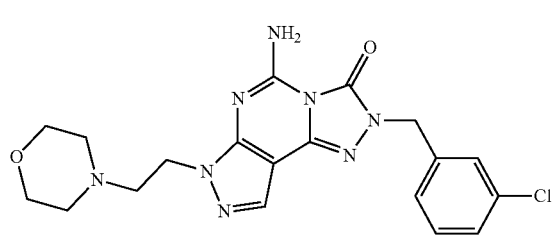

Using Step A from Example 12, substituting morpholine for dimethylamine, compound 18 was prepared.

Example 23

Preparation of Compound 19

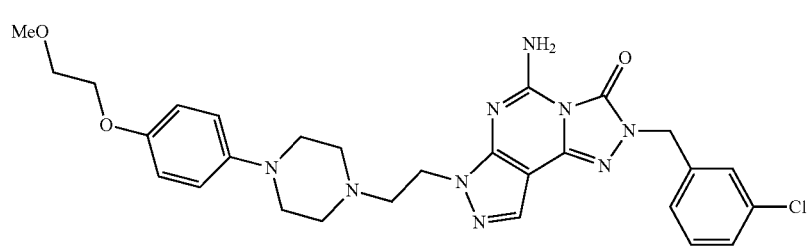

Using Step A from Example 12, substituting 1-(4-(2-methoxyethoxy)phenyl)piperazine for dimethylamine, compound 19 was prepared.

Example 24

Preparation of Compound 20

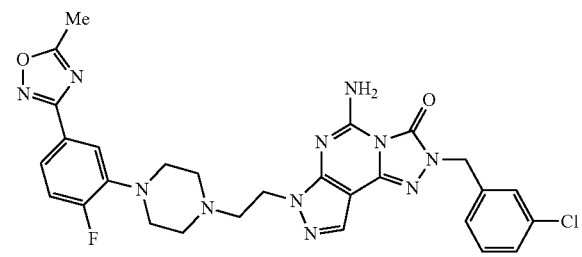

Using Step A from Example 12, substituting compound 9a for dimethylamine, compound 20 was prepared.

Example 25

Preparation of Compound 21

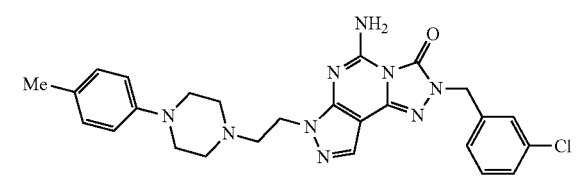

Using Step A from Example 12, substituting 1-p-tolylpiperazine for dimethylamine, compound 21 was prepared.

Example 26

Preparation of Compound 22

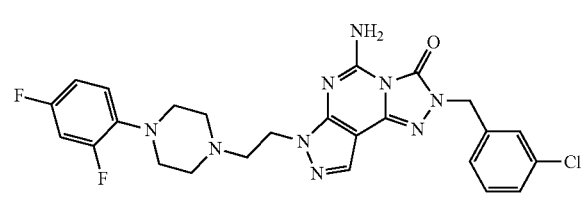

Using Step A from Example 12, substituting 1-(2,4-difluorophenyl)piperazine for dimethylamine, compound 22 was prepared.

Example 27

Preparation of Compound 24

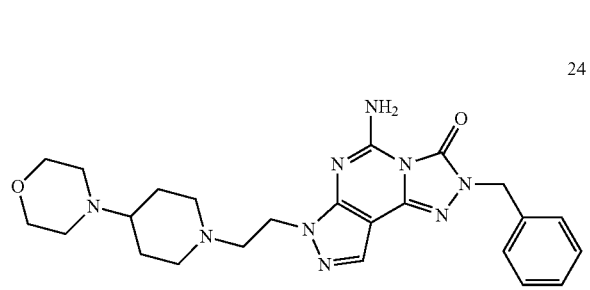

Using Step A from Example 12, substituting compound 5 for compound 8 and substituting 4-(piperidin-4-yl)-morpholine for dimethylamine, compound 24 was prepared.

Example 28

Preparation of Compound 25

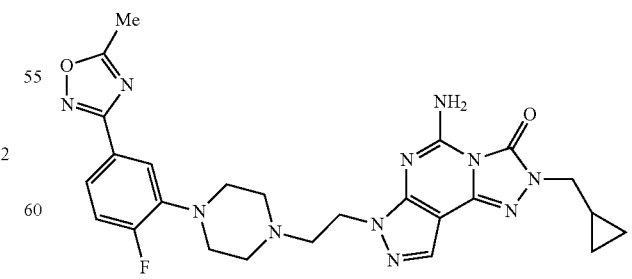

Using Step A from Example 12, substituting compound 28 for compound 8 and substituting compound 9a for dimethylamine, compound 25 was prepared.

Example 29

Preparation of Compound 26

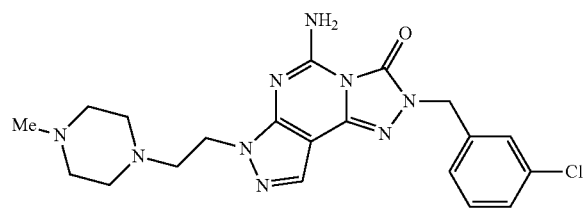

Using Step A from Example 12, substituting 1-methylpiperazine for dimethylamine, compound 26 was prepared.

Example 30

Preparation of Compound 30

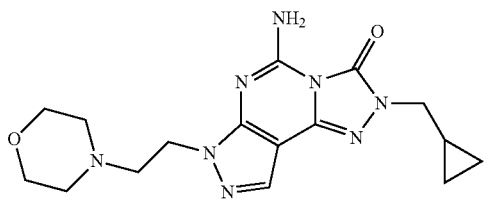

Using Step A from Example 12, substituting compound 28 for compound 8 and substituting morpholine for dimethylamine, compound 30 was prepared.

Example 31

Preparation of Compound 31

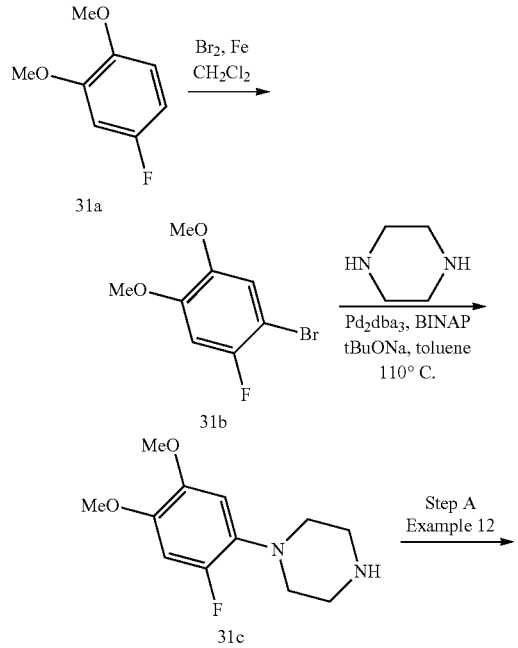

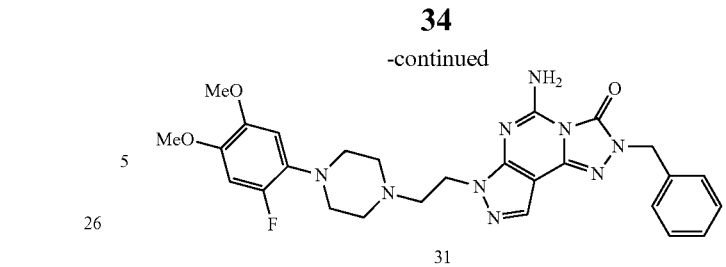

Step A—Synthesis of Compound 31b
To compound 31a (5.0 g, 32 mmol) was added $CH_2Cl_2$ (40 mL) and Fe powder (80 mg, 1.44 mmol) and to this solution $Br_2$ (1.8 mL, 35 mmol) in $CH_2Cl_2$ (20 mL) was added slowly and the solution was stirred for 4 h. Poured solution into $H_2O$ (100 mL), transferred to sep. funnel, separated layers, washed organic layer with 10% $NaOH_{aq}$, washed with $H_2O$, dried ($MgSO_4$), filtered, and concentrated to yield compound 31b (7.9 g, 100%).

Step B—Synthesis of Compound 31c
To compound 31b (2.0 g, 8.5 mmol) was added piperazine (4.4 g, 51 mmol), BINAP (318 mg, 0.51 mmol), $Pd_2dba_3$ (98 mg, 0.17 mmol), NaOtBu (1.14 g, 11.9 mmol), and toluene (15 mL). The solution was stirred and heated to 110° C. for 24 h. Allowed to cool, extracted solution with 1N HCl, basified with 1N NaOH to pH 12, extracted with $CH_2Cl_2$, dried ($MgSO_4$), filtered, and concentrated to yield compound 31c (1.9 g, 90%).

Step C—Synthesis of Compound 31
Using Step A from Example 12, substituting compound 5 for compound 8 and substituting compound 31c for dimethylamine, compound 31 was prepared.

Example 32

Preparation of Compound 32

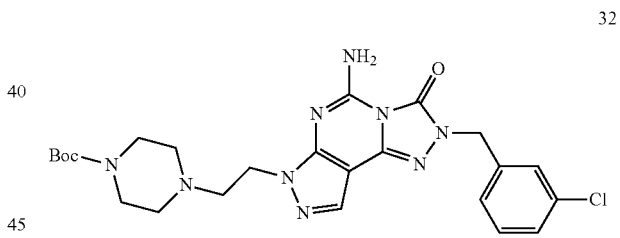

Using Step A from Example 12, substituting 1-Boc-piperazine for dimethylamine, compound 32 was prepared.

Example 33

Preparation of Compound 33

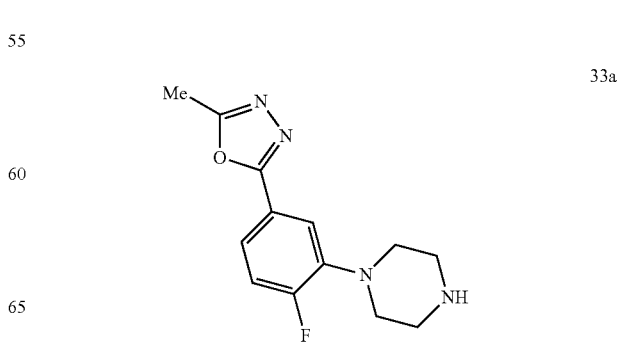

35
-continued

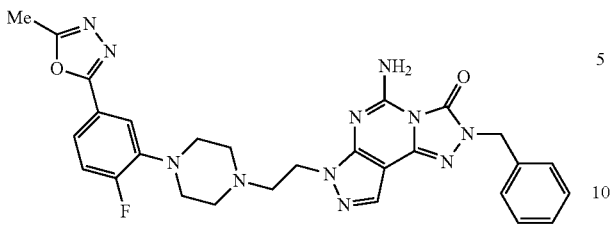

33

Using Step A from Example 12, substituting compound 5 for compound 8 and substituting compound 33a (patent US 2005/0239795A) for dimethylamine, compound 33 was prepared.

Example 34

Preparation of Compound 34

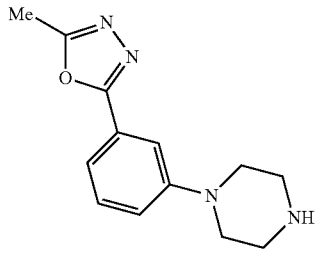

34a

36
-continued

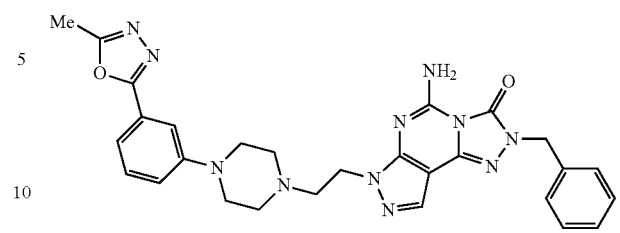

34

Using Step A from Example 12, substituting compound 5 for compound 8 and substituting compound 34a (patent US 2005/0239795A) for dimethylamine, compound 34 was prepared.

Example 35

LC/MS Data For Selected Compounds

LC/MS data for selected [1,2,4]triazolo[4,3-c]pyrimidin-3-one derivatives is provided below in Table 1, wherein the compound numbers correspond to the compound numbering set forth in the above specification.

TABLE 1

LC/MS Data For Selected [1,2,4]triazolo[4,3-c]pyrimidin-3-one Derivatives

| Compound No. | Compound Name | LCMS Calculated M + 1 | LCMS Observed M + 1 |
|---|---|---|---|
| 1 | 11-AMINO-4,5-DIHYDRO-2-(PHENYLMETHYL)BENZO[h][1,2,4]TRIAZOLO[4,3-c]QUINAZOLIN-1(2H)-ONE | 344.382 | 344.2 |
| 2 | 5-AMINO-7-PHENYL-2-(PHENYLMETHYL)-1,2,4-TRIAZOLO[4,3-c]PYRIMIDIN-3(2H)-ONE | 318.1 | 318.2 |
| 3 | 5-AMINO-7-(4-METHOXYPHENYL)-2-(PHENYLMETHYL)-1,2,4-TRIAZOLO[4,3-c]PYRIMIDIN-3(2H)-ONE | 348.1 | 348.2 |
| 4 | 5-AMINO-2-(PHENYLMETHYL)-7-(3-PYRIDINYL)-1,2,4-TRIAZOLO[4,3-c]PYRIMIDIN-3(2H)-ONE | 319.1 | 319.2 |
| 5 | 5-AMINO-7-ETHENYL-2,7-DIHYDRO-2-(PHENYLMETHYL)-3H-PYRAZOLO[4,3-e]-1,2,4-TRIAZOLO[4,3-c]PYRIMIDIN-3-ONE | 308.1 | 308.2 |
| 6 | 5-AMINO-2-[(3-CHLOROPHENYL)METHYL]-7-ETHENYL-2,7-DIHYDRO-3H-PYRAZOLO[4,3-e]-1,2,4-TRIAZOLO[4,3-c]PYRIMIDIN-3-ONE | 341.1 | 342.2 |
| 7 | 5-AMINO-7-(2-CHLOROETHYL)-2,7-DIHYDRO-2-(PHENYLMETHYL)-3H-PYRAZOLO[4,3-e]-1,2,4-TRIAZOLO[4,3-c]PYRIMIDIN-3-ONE | 344.1 | 344.2 |
| 8 | 5-AMINO-7-(2-CHLOROETHYL)-2-[(3-CHLOROPHENYL)METHYL]-2,7-DIHYDRO-3H-PYRAZOLO[4,3-e]-1,2,4-TRIAZOLO[4,3-c]PYRIMIDIN-3-ONE | 378.1 | 378.2 |
| 9 | 5-AMINO-7-[2-[4-[2-FLUORO-5-(5-METHYL-1,2,4-OXADIAZOL-3-YL)PHENYL]-1-PIPERAZINYL]ETHYL]-2,7-DIHYDRO-2-(PHENYLMETHYL)-3H-PYRAZOLO[4,3-e]-1,2,4-TRIAZOLO[4,3-c]PYRIMIDIN-3-ONE | 570.2 | 570.3 |
| 10 | 5-AMINO-2-[(3-CHLOROPHENYL)METHYL]-2,7-DIHYDRO-7-[2-[4-(4-MORPHOLINYL)-1-PIPERIDINYL]ETHYL]-3H-PYRAZOLO[4,3-e]-1,2,4-TRIAZOLO[4,3-c]PYRIMIDIN-3-ONE | 512.2 | 512.3 |

TABLE 1-continued

LC/MS Data For Selected [1,2,4]triazolo[4,3-c]pyrimidin-3-one Derivatives

| Compound No. | Compound Name | LCMS Calculated M + 1 | LCMS Observed M + 1 |
|---|---|---|---|
| 11 | 5-AMINO-7-[2-(1,4-DIOXA-8-AZASPIRO[4.5]DEC-8-YL)ETHYL]-2,7-DIHYDRO-2-(PHENYLMETHYL)-3H-PYRAZOLO[4,3-e]-1,2,4-TRIAZOLO[4,3-c]PYRIMIDIN-3-ONE | 451.2 | 451.2 |
| 12 | 1-[2-[5-AMINO-2,3-DIHYDRO-3-OXO-2-(PHENYLMETHYL)-7H-PYRAZOLO[4,3-e]-1,2,4-TRIAZOLO[4,3-c]PYRIMIDIN-7-YL]ETHYL]-4-[METHYLSULFONYL]PIPERAZINE | 472.1 | 472.3 |
| 13 | 5-AMINO-2,7-DIHYDRO-7-[2-(4-MORPHOLINYL)ETHYL]-2-(PHENYLMETHYL)-3H-PYRAZOLO[4,3-e]-1,2,4-TRIAZOLO[4,3-c]PYRIMIDIN-3-ONE | 395.2 | 395.2 |
| 14 | 1-[2-[5-AMINO-2-[(3-CHLOROPHENYL)METHYL]-2,3-DIHYDRO-3-OXO-7H-PYRAZOLO[4,3-e]-1,2,4-TRIAZOLO[4,3-c]PYRIMIDIN-7-YL]ETHYL]-4-(METHYLSULFONYL)PIPERAZINE | 506.1 | 506.3 |
| 15 | 5-AMINO-2-[(3-CHLOROPHENYL)METHYL]-7-[2-(1,4-DIOXA-8-AZASPIRO[4.5]DEC-8-YL)ETHYL]-2,7-DIHYDRO-3H-PYRAZOLO[4,3-e]-1,2,4-TRIAZOLO[4,3-c]PYRIMIDIN-3-ONE | 485.2 | 485.3 |
| 16 | 5-AMINO-2,7-DIHYDRO-2-(PHENYLMETHYL)-7-[2-(4-PYRAZINYL-1-PIPERAZINYL)ETHYL]-3H-PYRAZOLO[4,3-e]-1,2,4-TRIAZOLO[4,3-c]PYRIMIDIN-3-ONE | 472.2 | 472.3 |
| 17 | 5-AMINO-2-[(3-CHLOROPHENYL)METHYL]-2,7-DIHYDRO-7-[2-(4-PYRAZINYL-1-PIPERAZINYL)ETHYL]-3H-PYRAZOLO[4,3-e]-1,2,4-TRIAZOLO[4,3-c]PYRIMIDIN-3-ONE | 506.2 | 506.3 |
| 18 | 5-AMINO-2-[(3-CHLOROPHENYL)METHYL]-2,7-DIHYDRO-7-[2-(4-MORPHOLINYL)ETHYL]-3H-PYRAZOLO[4,3-e]-1,2,4-TRIAZOLO[4,3-c]PYRIMIDIN-3-ONE | 429.2 | 429.2 |
| 19 | 5-AMINO-2-[(3-CHLOROPHENYL)METHYL]-2,7-DIHYDRO-7-[2-[4-[4-(2-METHOXYETHOXY)PHENYL]-1-PIPERAZINYL]ETHYL]-3H-PYRAZOLO[4,3-e]-1,2,4-TRIAZOLO[4,3-c]PYRIMIDIN-3-ONE | 578.2 | 578.2 |
| 20 | 5-AMINO-2-[(3-CHLOROPHENYL)METHYL]-7-[2-[4-[2-FLUORO-5-(5-METHYL-1,2,4-OXADIAZOL-3-YL)PHENYL]-1-PIPERAZINYL]ETHYL]-2,7-DIHYDRO-3H-PYRAZOLO[4,3-e]-1,2,4-TRIAZOLO[4,3-c]PYRIMIDIN-3-ONE | 604.2 | 604.3 |
| 21 | 5-AMINO-2-[(3-CHLOROPHENYL)METHYL]-2,7-DIHYDRO-7-[2-[4-(4-METHYLPHENYL)-1-PIPERAZINYL]ETHYL]-3H-PYRAZOLO[4,3-e]-1,2,4-TRIAZOLO[4,3-c]PYRIMIDIN-3-ONE | 518.2 | 518.3 |
| 22 | 5-AMINO-2-[(3-CHLOROPHENYL)METHYL]-7-[2-[4-(2,4-DIFLUOROPHENYL)-1-PIPERAZINYL]ETHYL]-2,7-DIHYDRO-3H-PYRAZOLO[4,3-e]-1,2,4-TRIAZOLO[4,3-c]PYRIMIDIN-3-ONE | 540.2 | 540.3 |
| 23 | 5-AMINO-2-(CYCLOPROPYLMETHYL)-7-ETHENYL-2,7-DIHYDRO-3H-PYRAZOLO[4,3-e]-1,2,4-TRIAZOLO[4,3-c]PYRIMIDIN-3-ONE | 272.1 | 272.1 |
| 24 | 5-AMINO-2,7-DIHYDRO-7-[2-[4-(4-MORPHOLINYL)-1-PIPERIDINYL]ETHYL]-2-(PHENYLMETHYL)-3H-PYRAZOLO[4,3-e]-1,2,4-TRIAZOLO[4,3-c]PYRIMIDIN-3-ONE | 478.3 | 478.3 |
| 25 | 5-AMINO-2-(CYCLOPROPYLMETHYL)-7-[2-[4-[2-FLUORO-5-(5-METHYL-1,2,4-OXADIAZOL-3-YL)PHENYL]-1-PIPERAZINYL]ETHYL]-2,7-DIHYDRO-3H-PYRAZOLO[4,3-e]-1,2,4-TRIAZOLO[4,3-c]PYRIMIDIN-3-ONE | 534.2 | 534.3 |
| 26 | 5-AMINO-2-[(3-CHLOROPHENYL)METHYL]-2,7-DIHYDRO-7-[2-(4-METHYL-1-PIPERAZINYL)ETHYL]-3H-PYRAZOLO[4,3-e]-1,2,4-TRIAZOLO[4,3-c]PYRIMIDIN-3-ONE | 442.2 | 442.2 |
| 27 | 5-AMINO-2-[(3-CHLOROPHENYL)METHYL]-7-[2-(DIMETHYLAMINO)ETHYL]-2,7-DIHYDRO-3H-PYRAZOLO[4,3-e]-1,2,4-TRIAZOLO[4,3-c]PYRIMIDIN-3-ONE | 387.1 | 387.2 |
| 28 | 5-AMINO-7-(2-CHLOROETHYL)-2-(CYCLOPROPYLMETHYL)-2,7-DIHYDRO-3H-PYRAZOLO[4,3-e]-1,2,4-TRIAZOLO[4,3-c]PYRIMIDIN-3-ONE | 308.1 | 308.2 |

TABLE 1-continued

LC/MS Data For Selected [1,2,4]triazolo[4,3-c]pyrimidin-3-one Derivatives

| Compound No. | Compound Name | LCMS Calculated M + 1 | LCMS Observed M + 1 |
|---|---|---|---|
| 29 | 5-AMINO-2,7-DIHYDRO-2-PHENYL-7-(2-PHENYLETHYL)-3H-PYRAZOLO[4,3-e]-1,2,4-TRIAZOLO[4,3-c]PYRIMIDIN-3-ONE | 372.2 | 372.2 |
| 30 | 5-AMINO-2-(CYCLOPROPYLMETHYL)-2,7-DIHYDRO-7-[2-(4-MORPHOLINYL)ETHYL]-3H-PYRAZOLO[4,3-e]-1,2,4-TRIAZOLO[4,3-c]PYRIMIDIN-3-ONE | 359.2 | 359.2 |
| 31 | 5-AMINO-7-[2-[4-(2-FLUORO-4,5-DIMETHOXYPHENYL)-1-PIPERAZINYL]ETHYL]-2,7-DIHYDRO-2-(PHENYLMETHYL)-3H-PYRAZOLO[4,3-e]-1,2,4-TRIAZOLO[4,3-c]PYRIMIDIN-3-ONE | 548.3 | 548.3 |
| 32 | 1,1-DIMETHYLETHYL 4-[2-[5-AMINO-2-[(3-CHLOROPHENYL)METHYL]-2,3-DIHYDRO-3-OXO-7H-PYRAZOLO[4,3-e]-1,2,4-TRIAZOLO[4,3-c]PYRIMIDIN-7-YL]ETHYL]-1-PIPERAZINECARBOXYLATE | 528.2 | 528.3 |
| 33 | 5-AMINO-7-[2-[4-[2-FLUORO-5-(5-METHYL-1,3,4-OXADIAZOL-2-YL)PHENYL]-1-PIPERAZINYL]ETHYL]-2,7-DIHYDRO-2-(PHENYLMETHYL)-3H-PYRAZOLO[4,3-e]-1,2,4-TRIAZOLO[4,3-c]PYRIMIDIN-3-ONE | 570.2 | 570.3 |
| 34 | 5-AMINO-2,7-DIHYDRO-7-[2-[4-[3-(5-METHYL-1,3,4-OXADIAZOL-2-YL)PHENYL]-1-PIPERAZINYL]ETHYL]-2-(PHENYLMETHYL)-3H-PYRAZOLO[4,3-e]-1,2,4-TRIAZOLO[4,3-c]PYRIMIDIN-3-ONE | 552.3 | 552.3 |

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses of organic origin, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of Formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

In this specification, the term "at least one compound of Formula I" (or a pharmaceutically acceptable salt, solvate, ester or prodrug thereof) means that one to three different compounds of Formula I (or pharmaceutically acceptable salt, solvate, ester or prodrug thereof) may be used in a pharmaceutical composition or method of treatment. Preferably one compound of Formula I or pharmaceutically acceptable salt, solvate, ester or prodrug thereof is used. Similarly, "one or more agents useful in the treatment of Parkinson's disease" means that one to three different agents, preferably one agent, may be used in a pharmaceutical composition or method of treatment. Preferably, one agent is used in combination with one compound of Formula I or pharmaceutically acceptable salt, solvate, ester or prodrug thereof.

The pharmacological activity of the compounds of the invention was determined by the following in vitro assays to measure $A_{2a}$ receptor activity.

Human Adenosine $A_{2a}$ and $A_1$ Receptor Competition Binding Assay Protocol
Membrane Sources:
$A_{2a}$: Human $A_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers:
Membrane dilution buffer: Dulbecco's Phosphate Buffered Saline (Gibco/BRL)+10 mM $MgCl_2$.
Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.
Ligands:
$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.
$A_1$: [3H]-DPCPX, AmershamPharmacia Biotech, Piscataway, N.J. Stock is prepared at 2 nM in membrane dilution buffer. Final assay concentration is 1 nM.
Non-Specific Binding:
$A_{2a}$: To determine non-specific binding, add 100 nM CGS15923 (RBI, Natick, Mass.). Working stock is prepared at 400 nM in compound dilution buffer.
$A_1$: To determine non-specific binding, add 100 μM NECA (RBI, Natick, Mass.). Working stock is prepared at 400 μM in compound dilution buffer.
Compound Dilution:
Prepare 1 mM stock solutions of compounds in 100% DMSO. Dilute in compound dilution buffer. Test at 10 concentrations ranging from 3 μM to 30 pM. Prepare working solutions at 4× final concentration in compound dilution buffer.
Assay Procedure:
Perform assays in deep well 96 well plates. Total assay volume is 200 μl. Add 50 μl compound dilution buffer (total ligand binding) or 50 μl CGS 15923 working solution ($A_{2a}$ non-specific binding) or 50 μl NECA working solution ($A_1$ non-specific binding) or 50 μl of drug working solution. Add 50 μl ligand stock ([3H]-SCH 58261 for $A_{2a}$, [3H]-DPCPX for $A_1$). Add 100 μl of diluted membranes containing the appropriate receptor. Mix. Incubate at room temperature for 90 minutes. Harvest using a Brandel cell harvester onto Packard GF/B filter plates. Add 45 μl Microscint 20 (Packard), and count using the Packard TopCount Microscintillation Counter. Determine $IC_{50}$ values by fitting the displacement curves using an iterative curve fitting program (Excel). Determine $K_i$ values using the Cheng-Prusoff equation.

Using the above test procedures, the following results were obtained for preferred and/or representative compounds of the invention.

Results of the binding assay on compounds of the invention showed $A_{2a}$ $K_i$ values of 0.3 to 791 nM, with preferred compounds showing $K_i$ values between 0.3 and 5.0 nM. Selectivity is determined by dividing $K_i$ for $A_1$ receptor by $K_i$ for $A_2$ receptor. Preferred compounds of the invention have a selectivity ranging from about 100 to about 1500.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the' judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of Formula I and a dopaminergic agent is administered, lower doses of the components will be effective compared to the doses of the components administered as monotherapy.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural Formula I:

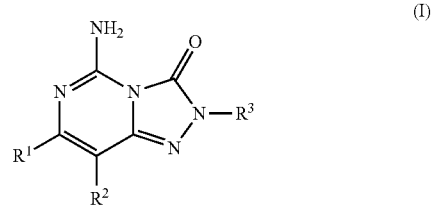

wherein:
$R^1$ represents aryl or heteroaryl; and
$R^2$ represents hydrogen; or
$R^1$ and $R^2$ together with the carbon atoms to which they are bonded form a further heterocyclic ring of the formula:

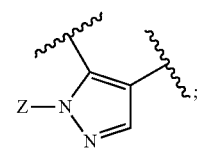

or a carbocyclic ring system of the formula:

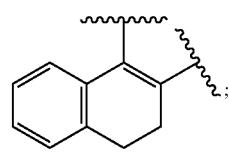

$R^3$ represents aryl, cycloalkylalkyl, aralkyl or heteroarylalkyl;
Z represents alkyl, alkenyl, haloalkyl, aminoalkyl, alkylaminoalkyl, dialkylaminoalkyl, aralkyl or $CH_2CH_2R^4$;

R⁴ represents a member selected from the group consisting of:

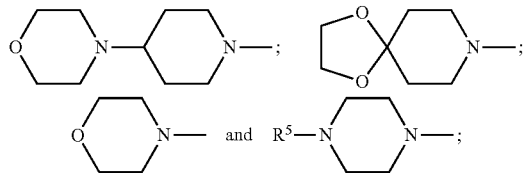

and

R⁵ represents alkyl, alkoxycarbonyl, alkylsulfonyl, aryl or heteroatyl; or a pharmaceutically acceptable salt, ester or prodrug of said compound of Formula I.

2. The compound of claim 1, or a pharmaceutically acceptable salt, ester or prodrug thereof, wherein R¹ represents aryl; and R² represents hydrogen.

3. The compound of claim 1, or a pharmaceutically acceptable salt, ester or prodrug thereof, wherein R¹ and R² together with the carbon atoms to which they are bonded form a further heterocyclic ring of the formula:

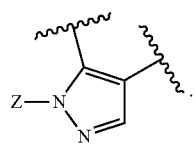

4. The compound of claim 1, or a pharmaceutically acceptable salt, ester or prodrug thereof, wherein R¹ and R² together with the carbon atoms to which they are bonded form a carbocyclic ring system of the formula:

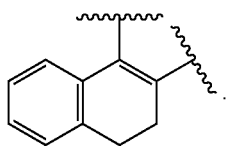

5. The compound of claim 1, or a pharmaceutically acceptable salt, ester or prodrug thereof, wherein:

R¹ represents aryl; and
R² represents hydrogen; or
R¹ and R² together with the carbon atoms to which they are bonded form a further heterocyclic ring of the formula:

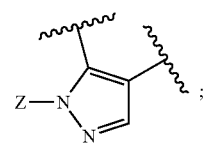

or a carbocyclic ring system of the formula:

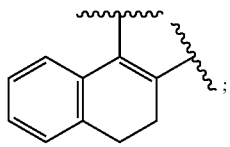

R³ represents aralkyl; and
Z represents alkenyl or haloalkyl.

6. A compound selected from the group consisting of:

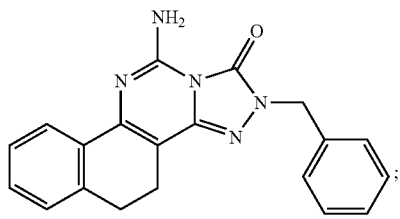

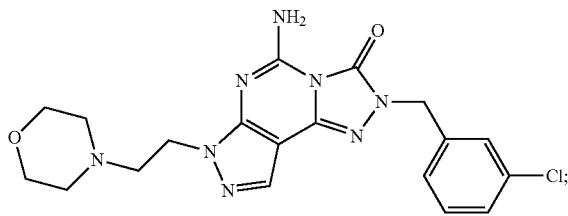

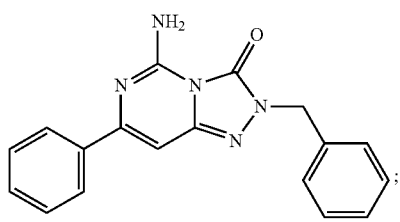

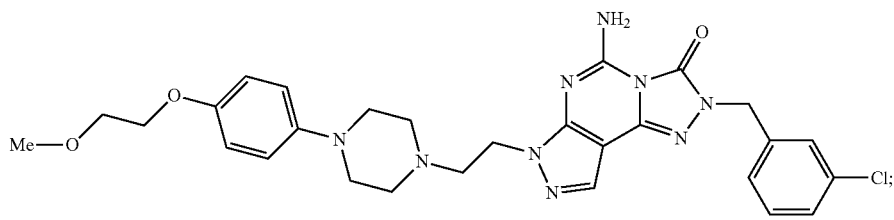

-continued
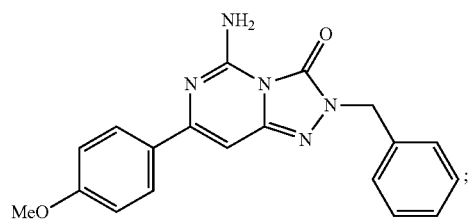
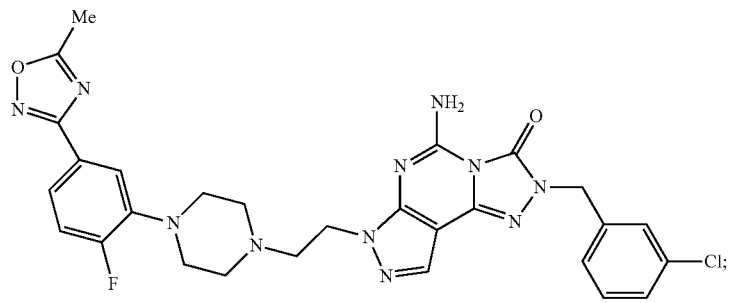
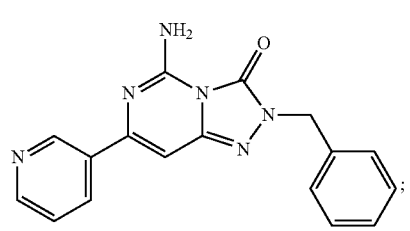
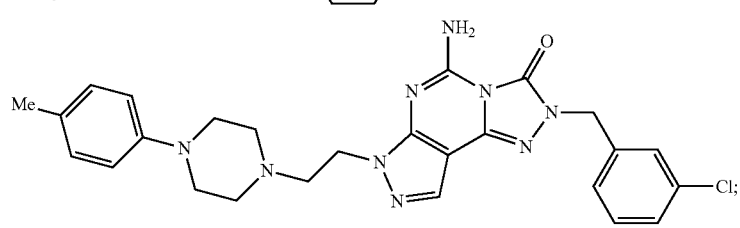
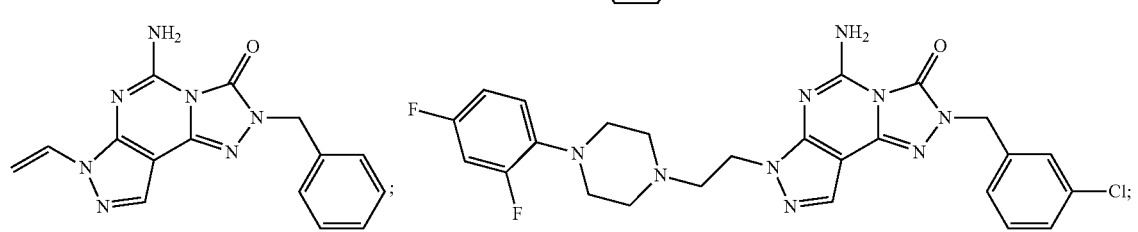
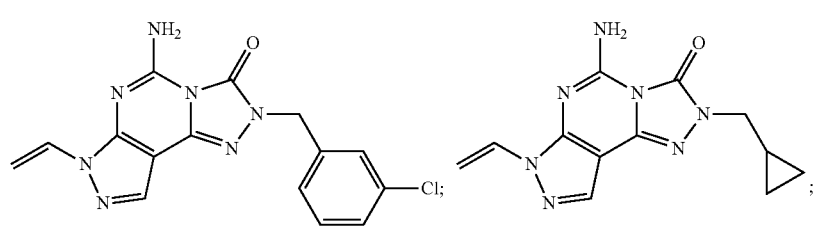
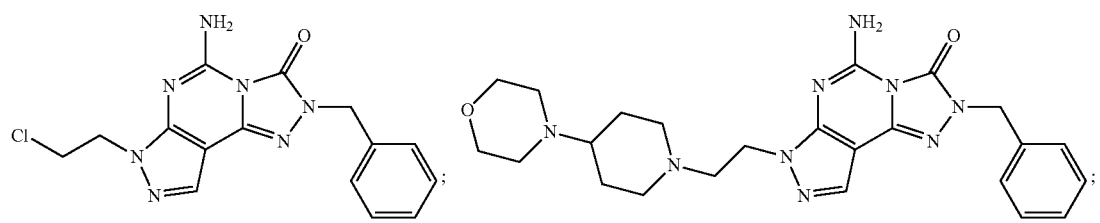

-continued
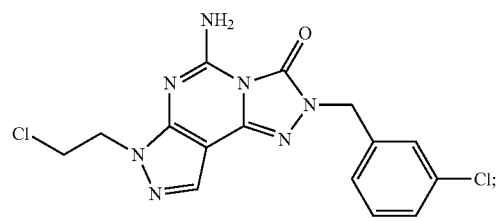
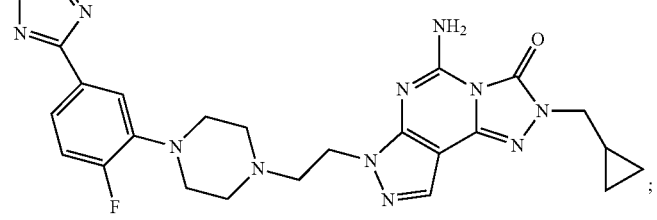
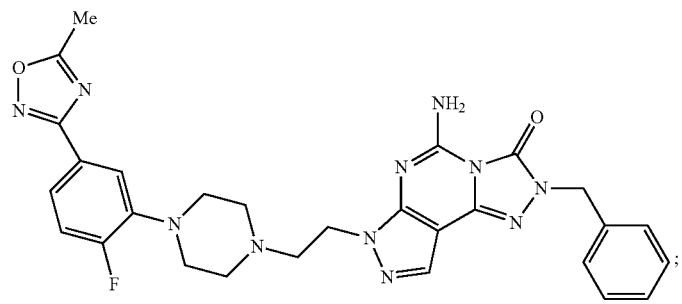
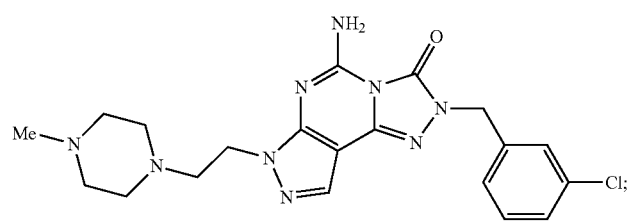
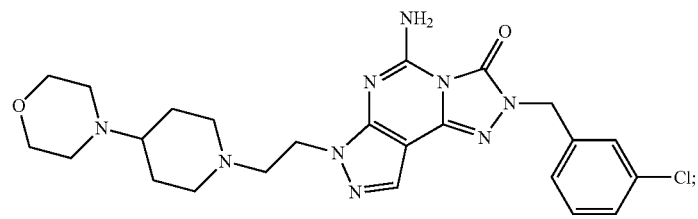
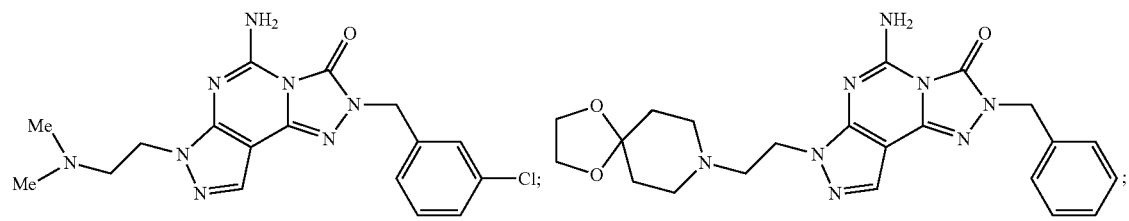
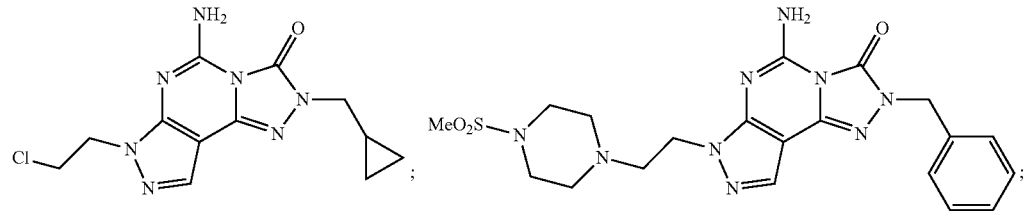
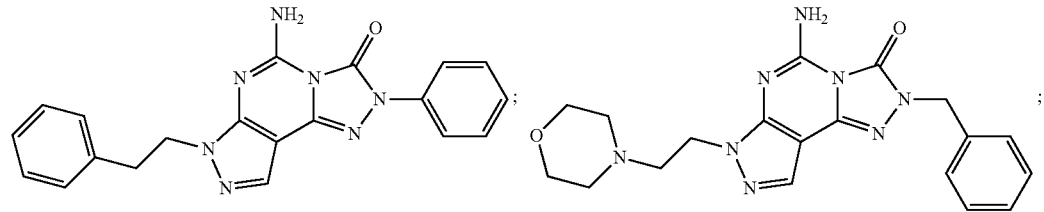

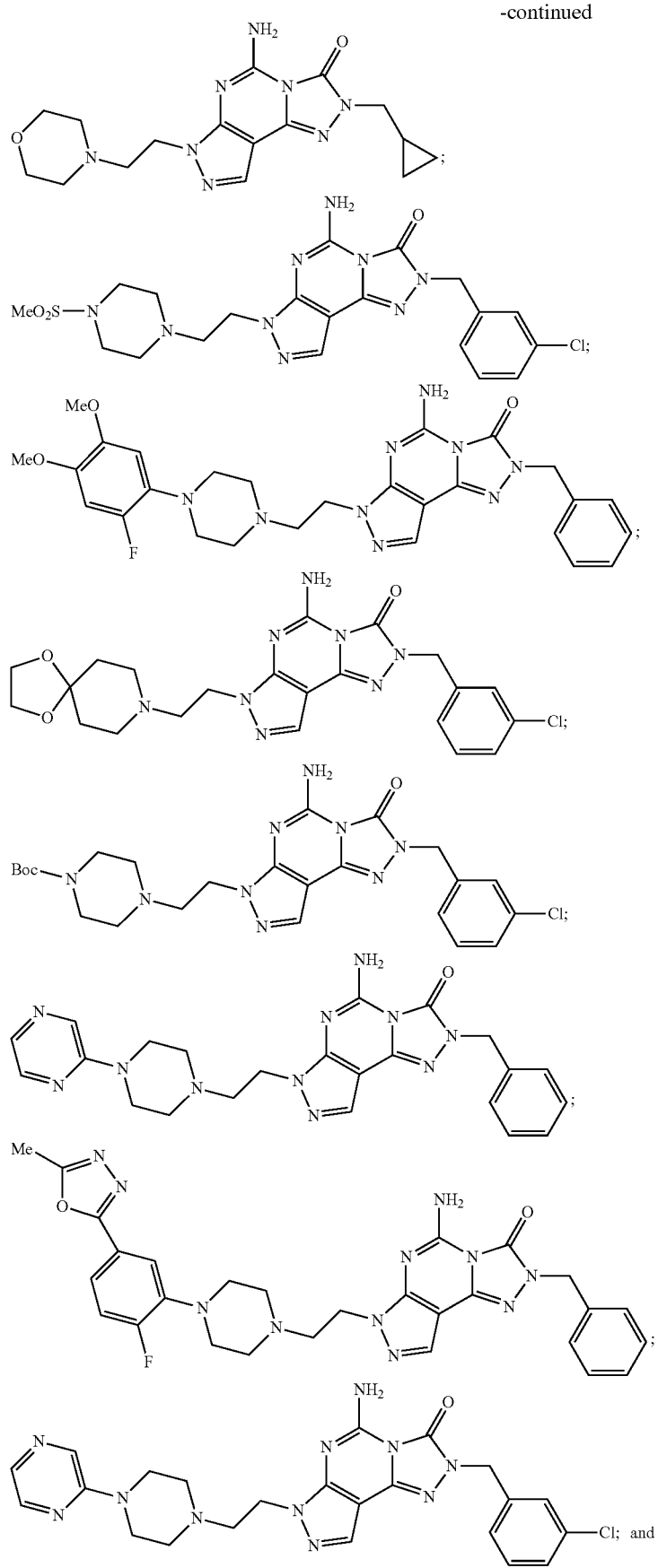

-continued

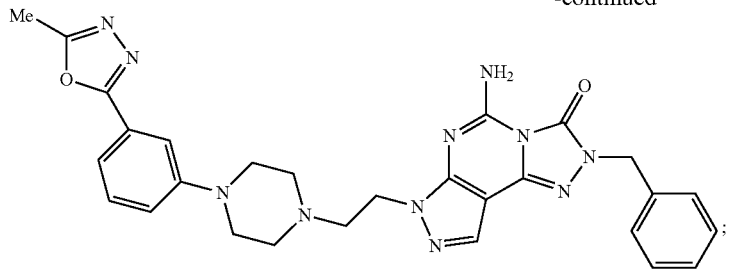

or a pharmaceutically acceptable salt, ester or prodrug thereof.

7. A pharmaceutical composition comprising at least one compound of claim 1, or a pharmaceutically acceptable salt, ester or prodrug thereof and at least one pharmaceutically acceptable carrier, adjuvant or vehicle.

8. A pharmaceutical composition comprising at least one compound of claim 6, or a pharmaceutically acceptable salt, ester or prodrug thereof and at least one pharmaceutically acceptable carrier, adjuvant or vehicle.

9. The pharmaceutical composition of claim 7, further comprising one or more additional therapeutic agents.

10. The pharmaceutical composition of claim 8, further comprising one or more additional therapeutic agents.

11. The pharmaceutical composition of claim 9, wherein the one or more additional therapeutic agents are one or more therapeutic agents useful for the treatment of Parkinson's Disease.

12. The pharmaceutical composition of claim 10, wherein the one or more additional therapeutic agents are one or more therapeutic agents useful for the treatment of Parkinson's disease.

13. The pharmaceutical composition of claim 11, wherein the one or more therapeutic agents useful for the treatment of Parkinson's disease are one or more therapeutic agents selected from the group consisting of L-DOPA, dopaminergic agonists, MAO-B inhibitors, DOPA decarboxylase inhibitors and COMT inhibitors.

14. The pharmaceutical composition of claim 12, wherein the one or more therapeutic agents useful for the treatment of Parkinson's disease are one or more therapeutic agents selected from the group consisting of L-DOPA, dopaminergic agonists, MAO-B inhibitors, DOPA decarboxylase inhibitors and COMT inhibitors.

15. A method of treating a disease of the central nervous system or stroke, comprising administering an effective amount therefor of a compound of claim 1 or a pharmaceutically acceptable salt, ester or prodrug thereof to a mammal in need of such treatment.

16. The method of claim 15, wherein the disease of the central nervous system is depression, a cognitive disease or a neurodegenerative disease.

17. The method of claim 15, wherein the disease of the central nervous system is Parkinson's disease, senile dementia, a psychosis of organic origin, attention deficit disorder, Extra Pyramidal Syndrome, dystonia, restless leg syndrome or periodic limb movement in sleep.

18. A method of treating Parkinson's disease comprising administering an effective amount therefor of a pharmaceutical composition according to claim 7 to a mammal in need thereof.

19. The method of claim 18, wherein the pharmaceutical composition comprises a therapeutically effective amount of a compound selected from the group consisting of:

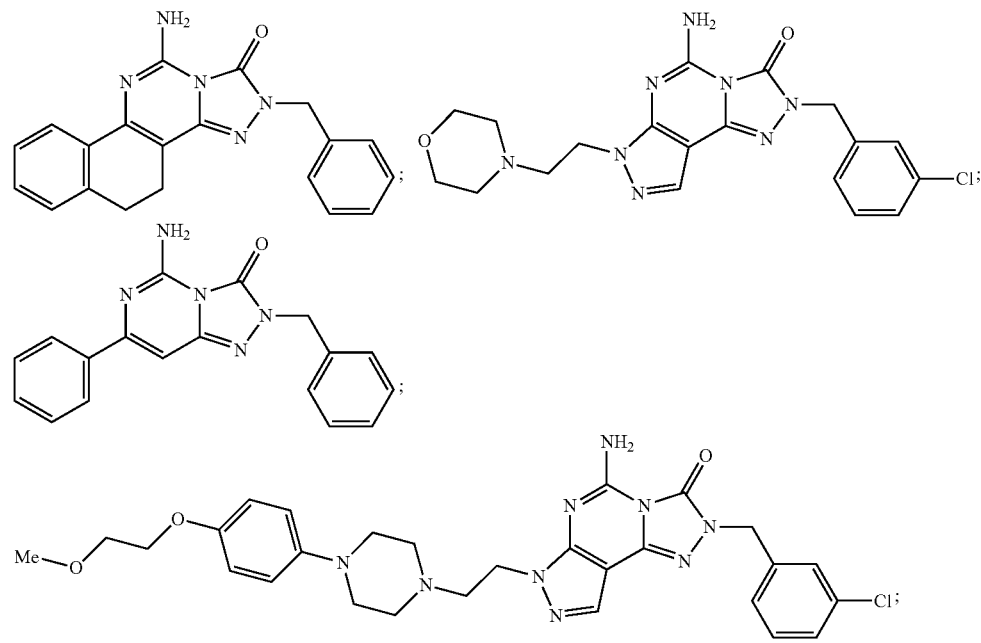

-continued
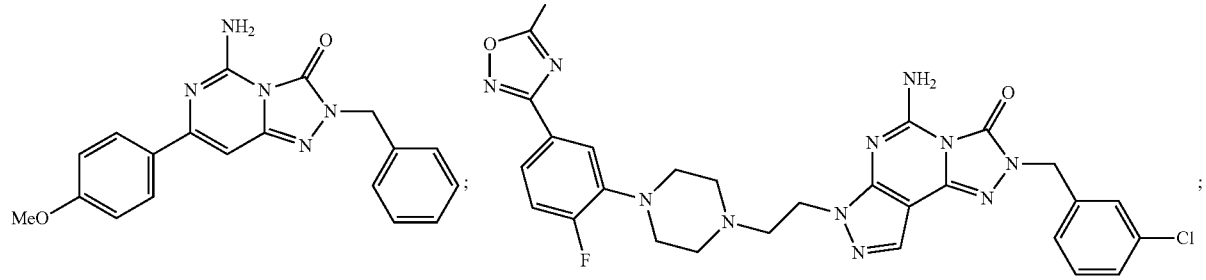
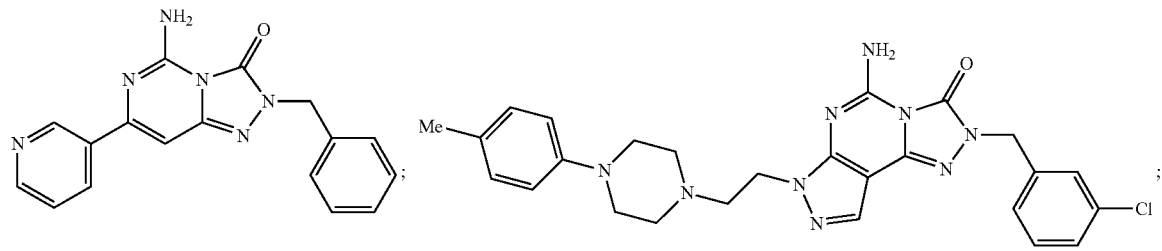
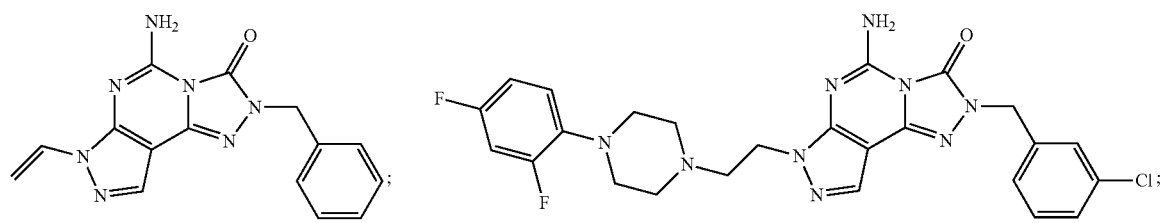
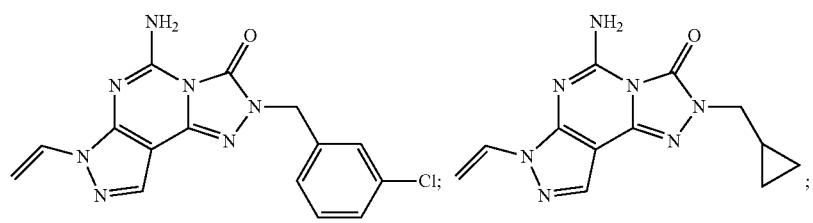
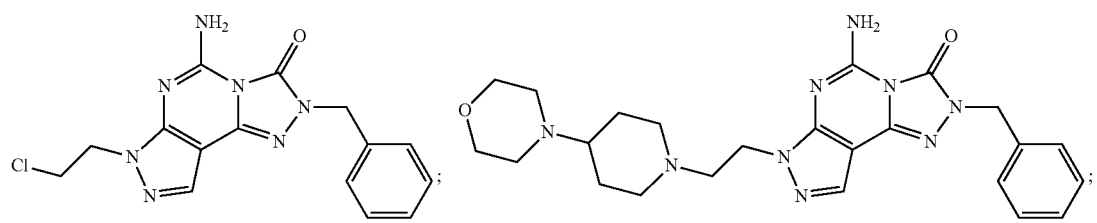
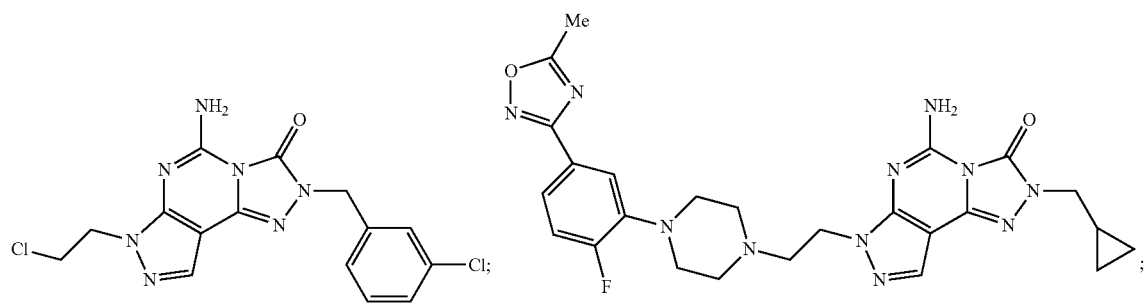

-continued
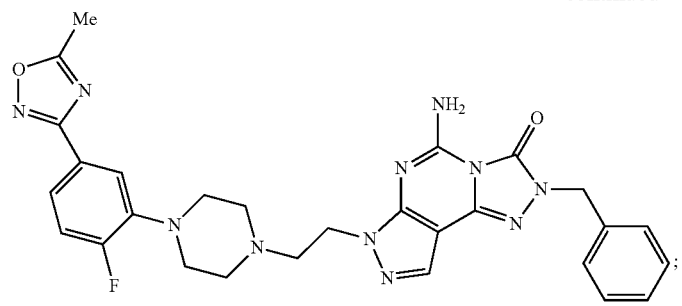
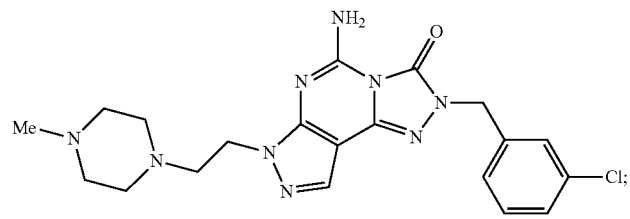
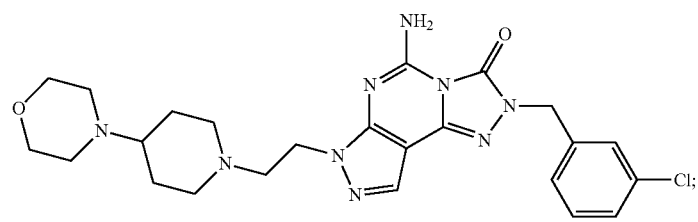
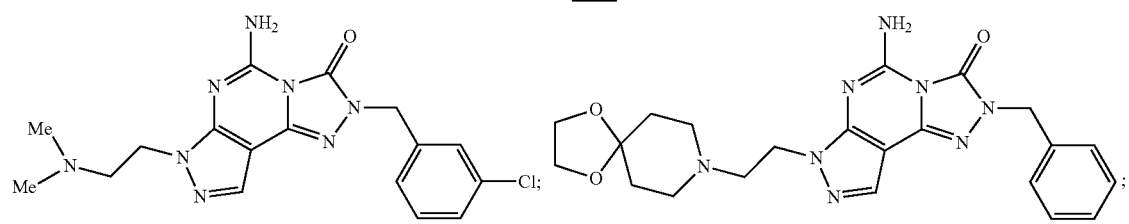
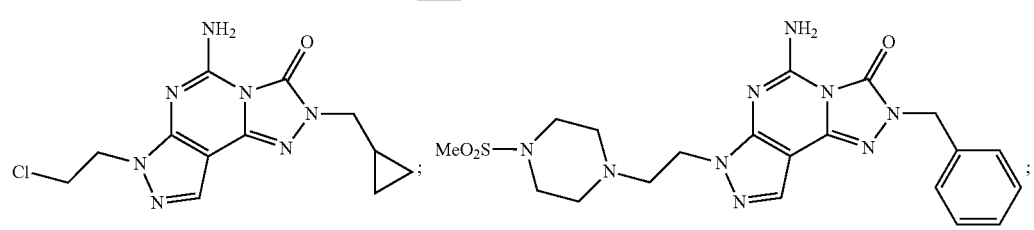
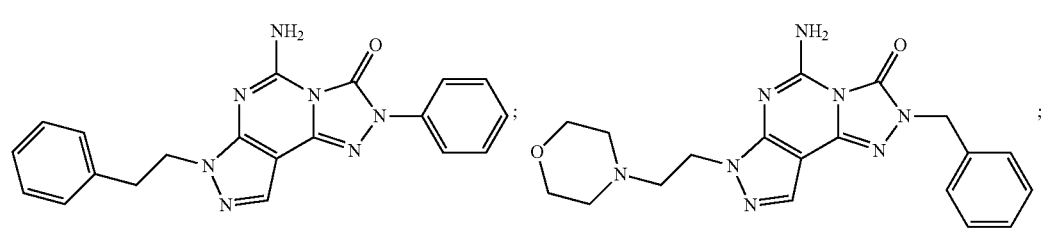
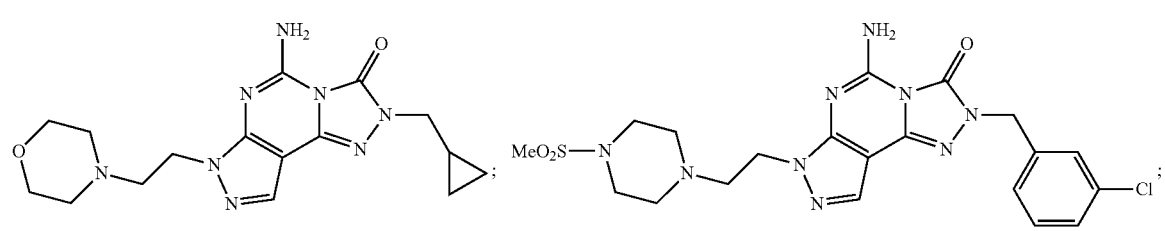

-continued
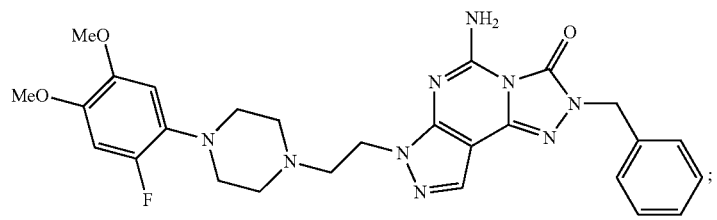
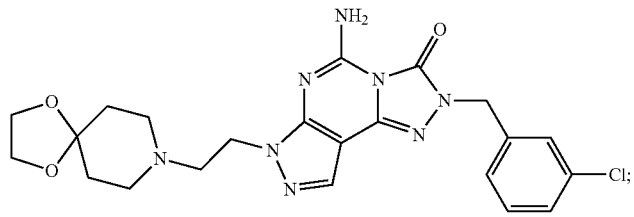
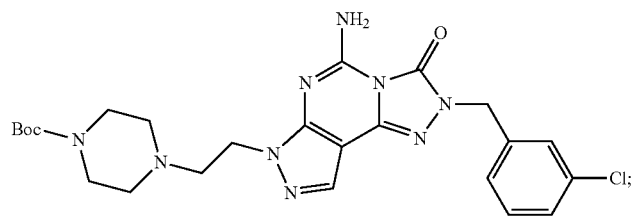
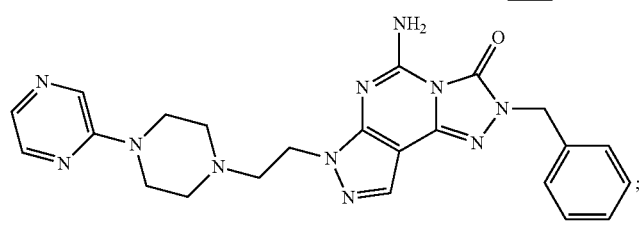
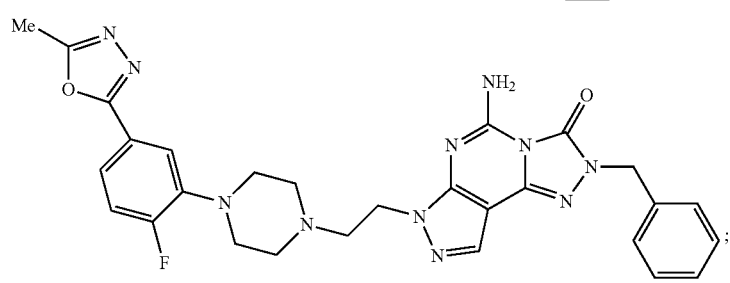
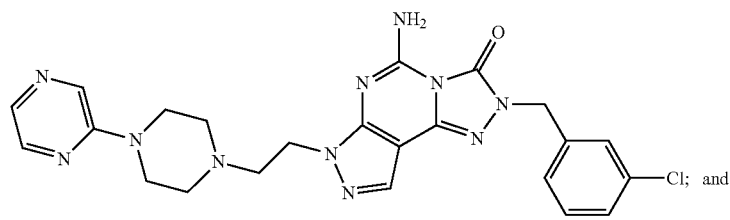
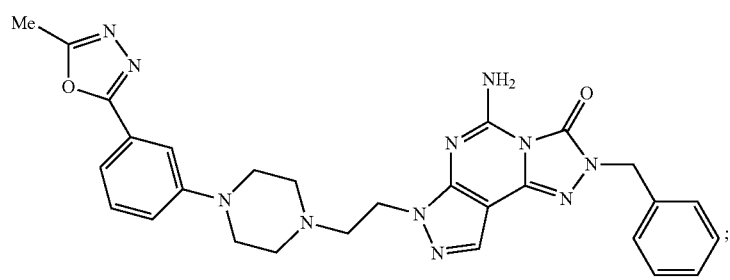

or a pharmaceutically acceptable salt, solvate, ester or prodrug thereof.

20. The method of claim 18, wherein the pharmaceutical composition additionally comprises one or more additional therapeutic agents are one or more therapeutic agents useful for the treatment of Parkinson's disease.

21. The method of claim 20, wherein the one or more therapeutic agents useful for the treatment of Parkinson's disease are one or more therapeutic agents selected from the group consisting of L-DOPA, dopaminergic agonists, MAO-B inhibitors, DOPA decarboxylase inhibitors and COMT inhibitors.

* * * * *